US012611558B2

(12) United States Patent　(10) Patent No.: US 12,611,558 B2

Gandrud et al.　(45) Date of Patent:　Apr. 28, 2026

(54) DIGITAL CHANGE MANAGEMENT SYSTEM FOR RESPIRATOR FILTER CARTRIDGES

(71) Applicant: 3M INNOVATIVE PROPERTIES COMPANY, St. Paul, MN (US)

(72) Inventors: Jonathan D. Gandrud, Woodbury, MN (US); Steven T. Awiszus, Woodbury, MN (US); Shane A. Hainey, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 755 days.

(21) Appl. No.: 18/002,298

(22) PCT Filed: May 21, 2021

(86) PCT No.: PCT/IB2021/054438

§ 371 (c)(1),
(2) Date: Dec. 19, 2022

(87) PCT Pub. No.: WO2021/255549

PCT Pub. Date: Dec. 23, 2021

(65) Prior Publication Data

US 2023/0347187 A1　Nov. 2, 2023

Related U.S. Application Data

(60) Provisional application No. 63/041,363, filed on Jun. 19, 2020.

(51) Int. Cl.
*A62B 18/08*　(2006.01)
*A62B 9/00*　(2006.01)
(Continued)

(52) U.S. Cl.
CPC ............ *A62B 18/088* (2013.01); *A62B 9/006* (2013.01); *A62B 18/006* (2013.01); *A62B 18/08* (2013.01);
(Continued)

(58) Field of Classification Search
CPC ..... A62B 18/088; A62B 9/006; A62B 18/006; A62B 19/00; A62B 18/08; A62B 23/02;
(Continued)

(56) References Cited

U.S. PATENT DOCUMENTS

| | | | | |
|---|---|---|---|---|
| 4,590,951 | A | * | 5/1986 | O'Connor ............ A62B 18/006 |
| | | | | 128/205.12 |
| 5,413,097 | A | * | 5/1995 | Birenheide .............. A62B 7/10 |
| | | | | 128/206.17 |

(Continued)

FOREIGN PATENT DOCUMENTS

| | | |
|---|---|---|
| CN | 106897795 A | 6/2017 |
| WO | 200951896 A3 | 4/2009 |

(Continued)

OTHER PUBLICATIONS

Extended European Search Report, EP 21 82 6878, Jun. 19, 2024, 2 pages.

(Continued)

*Primary Examiner* — Tu A Vo
(74) *Attorney, Agent, or Firm* — Katherine M. Scholz

(57) ABSTRACT

A filter cartridge for a respirator includes an RFID chip encoding a digital change management policy (DCMP) indicating a useful lifespan of the cartridge, so that the cartridge may be replaced at the end of the useful lifespan. In some examples, a system includes a respirator including a facepiece and an air blower; a removable contaminant capture cartridge installed within the respirator and config- (Continued)

ured to remove contaminants from the air as the air passes through the contaminant capture cartridge.

17 Claims, 5 Drawing Sheets

(51) Int. Cl.

| | | |
|---|---|---|
| *A62B 18/00* | (2006.01) | |
| *A62B 19/00* | (2006.01) | |
| *G16H 40/40* | (2018.01) | |
| *H04L 67/12* | (2022.01) | |

(52) U.S. Cl.
CPC ............. *A62B 19/00* (2013.01); *G16H 40/40* (2018.01); *H04L 67/12* (2013.01)

(58) Field of Classification Search
CPC ........ G16H 20/40; G16H 40/40; H04L 67/12; A41D 13/11–1192
See application file for complete search history.

(56) References Cited

U.S. PATENT DOCUMENTS

| | | | |
|---|---|---|---|
| 6,040,777 | A | 3/2000 | Ammann et al. |
| 6,186,140 | B1 * | 2/2001 | Hoague .............. B01D 46/0091 |
| | | | 128/201.25 |
| 6,294,997 | B1 | 9/2001 | Paratore et al. |
| 6,295,423 | B1 | 9/2001 | Haines et al. |
| 6,302,527 | B1 | 10/2001 | Walker |
| 6,853,303 | B2 | 2/2005 | Chen et al. |
| 8,294,580 | B2 | 10/2012 | Witwer et al. |
| 9,079,049 | B2 | 7/2015 | Tobias et al. |
| 10,835,704 | B1 * | 11/2020 | Heimbuch ........... A62B 18/025 |
| 2004/0215452 | A1 * | 10/2004 | Pearah ................... H04R 1/086 |
| | | | 704/E15.045 |
| 2005/0114154 | A1 | 5/2005 | Wolkowicz et al. |

| | | | |
|---|---|---|---|
| 2009/0006006 | A1 | 1/2009 | Bauer et al. |
| 2009/0055987 | A1 * | 3/2009 | Becker .................... A61F 9/068 |
| | | | 2/209.13 |
| 2009/0266361 | A1 * | 10/2009 | Bilger .................. A62B 18/006 |
| | | | 128/204.21 |
| 2010/0153023 | A1 * | 6/2010 | Parham .............. B01D 53/0415 |
| | | | 702/34 |
| 2010/0294273 | A1 * | 11/2010 | Rakow ................... A62B 19/00 |
| | | | 128/205.27 |
| 2011/0227700 | A1 | 9/2011 | Hamerly et al. |
| 2012/0055815 | A1 * | 3/2012 | Truex ..................... A62B 27/00 |
| | | | 206/205 |
| 2016/0001102 | A1 * | 1/2016 | Huh .......................... A62B 7/10 |
| | | | 128/206.17 |
| 2016/0236014 | A1 | 8/2016 | Ehler et al. |
| 2017/0368381 | A1 | 12/2017 | Awiszus et al. |
| 2017/0372216 | A1 * | 12/2017 | Awiszus ................. A61F 11/06 |
| 2018/0001049 | A1 * | 1/2018 | Schuller ............. B01D 53/0415 |
| 2018/0001120 | A1 * | 1/2018 | Virr ...................... B01D 46/009 |
| 2018/0108236 | A1 * | 4/2018 | Kanukurthy ......... G06Q 50/265 |
| 2018/0311517 | A1 * | 11/2018 | Patil ...................... A62B 18/02 |
| 2020/0282242 | A1 * | 9/2020 | Virr .......................... A62B 7/10 |

FOREIGN PATENT DOCUMENTS

| | | | | |
|---|---|---|---|---|
| WO | WO-2014191409 | A1 * | 12/2014 | ........... A62B 18/006 |
| WO | 2015143413 | A1 | 9/2015 | |
| WO | 2016115707 | A1 | 7/2016 | |
| WO | 2017040397 | A1 | 3/2017 | |
| WO | WO-2018087378 | A2 * | 5/2018 | ............. A41D 27/28 |
| WO | WO-2018106258 | A1 * | 6/2018 | ............. A62B 9/006 |
| WO | 2020128952 | A2 | 6/2020 | |

OTHER PUBLICATIONS

International Search Report for PCT International Application No. PCT/IB21/54438, mailed on Aug. 12, 2021, 2 pages.

* cited by examiner

DIGITAL CHANGE MANAGEMENT SYSTEM FOR RESPIRATOR FILTER CARTRIDGES

CROSS REFERENCE TO RELATED APPLICATIONS

This application is a national stage filing under 35 U.S.C. 371 of PCT/IB2021/054438, filed May 21, 2021, which claims the benefit of U.S. Provisional Application No. 63/041,363, filed Jun. 19, 2020, the disclosure of which is incorporated by reference in its/their entirety herein.

TECHNICAL FIELD

The present disclosure relates to personal protective equipment.

BACKGROUND

Many work environments include hazards that may expose people working within a given environment to a safety event, such as a fall, breathing contaminated air, or temperature-related injuries (e.g., heat stroke, frostbite, etc.). In many work environments, workers may utilize personal protective equipment (PPE) to help mitigate the risk of a safety event.

SUMMARY

In general, the present disclosure describes systems including contaminant capture cartridges, such as removable filter cartridges, for respirator devices such as a powered air purifying respirator (PAPR). According to examples of this disclosure, the cartridges include an integrated electronic chip or chipset, such as a radio-frequency identification device (RFID) tag having an antenna and a low-power integrated circuit (referred to herein as an RFID chip), configured to encode or otherwise store data that can be wirelessly accessed by an RFID-enabled computing device or system. In one example, a computing system is configured to retrieve, from a centralized repository, and encode onto the RFID chip, a digital change management policy (DCMP) that defines one or more rules for determining when the particular cartridge should be replaced, for example, at the end of the cartridge's useful lifespan. A particular policy written onto the RFID chip of a contaminant-capture cartridge may be both cartridge-specific (e.g., unique to a particular manufacturer and/or model type of the cartridge) and environment-specific, for example, driven by regulatory safety standards of a geographic region and/or work environment where the cartridge is intended to be used.

In some examples, the computing system may also encode usage data within the RFID chip of a particular cartridge, indicating an actual or current amount of use of the corresponding cartridge. For example, the computing system may periodically update the usage data indicating the actual amount of use within the RFID chip while the cartridge is installed within a respirator. Based on the actual amount of use and the DCMP, the computing device may periodically determine a remaining useful lifespan of the cartridge, for example, an amount of use remaining before the cartridge needs to be replaced, according to the DCMP. In some cases, the computing device may determine that the actual amount of use of the cartridge is above a predetermined threshold amount of use (e.g., above 90% of the useful lifespan of the cartridge), and output a notification that the cartridge may need to be replaced.

In this way, techniques of this disclosure may enable technical solutions for both more-efficiently managing resources and increasing worker safety. For example, by encoding a DMCP directly within the article of personal protective equipment (PPE) to which it pertains, the DMCP can be specifically tailored to both the type of PPE and the environment in which the PPE is to be used, thereby enabling highly accurate monitoring of the useful lifespan of the article of PPE. This highly accurate monitoring helps inform and discourage a user from replacing the PPE too early (e.g., before the useful lifespan has been expended), thereby reducing waste of precious resources. Similarly, highly accurate usage monitoring helps inform and potentially discourage a user from replacing the PPE too late (e.g., after the cartridges have begun to exhibit reduced performance), thereby increasing the safety of the worker using the respirator. In some examples, the tailored DCMPs may be used to control alerting and other data output (e.g., such as a time-sensitive use counter, a visual display, or other usage-data messages), or other operations of the PPE.

In one example, the disclosure describes a system that includes a respirator having a facepiece configured to form a sealed area over a nose and mouth of a user, and an air blower coupled to the facepiece by a hose to supply air to the sealed area: a removable contaminant capture cartridge installed within the respirator and configured to remove contaminants from the air as the air passes through the contaminant capture cartridge, wherein the contaminant capture cartridge comprises an electronic chip or chipset encoding a digital change management policy (DCMP) indicating a useful lifespan of the contaminant capture cartridge; and a computing device configured to write the DCMP onto the RFID chip or read the DCMP from the electronic chip or chipset.

In another example, the disclosure describes a removable contaminant capture cartridge device configured to be installed within a respirator, wherein the contaminant capture cartridge is configured to remove contaminants from air as the air passes through the contaminant capture cartridge; and wherein the contaminant capture cartridge includes an electronic chip or chipset encoding a digital change management policy (DCMP) indicating a useful lifespan of the contaminant capture cartridge.

In another example, the disclosure describes a method that includes reading, by a computing device, a model number encoded within an electronic chip or chipset of a removable contaminant capture cartridge configured to be installed within a respirator: retrieving, by the computing device based on the model number: a digital change management policy (DCMP) indicating a useful lifespan of the contaminant capture cartridge; and encoding, by the computing device, the DCMP within the electronic chip or chipset.

The details of one or more examples of the disclosure are set forth in the accompanying drawings and the description below. Other features, objects, and advantages of the disclosure will be apparent from the description and drawings, and from the claims.

Figure 1:
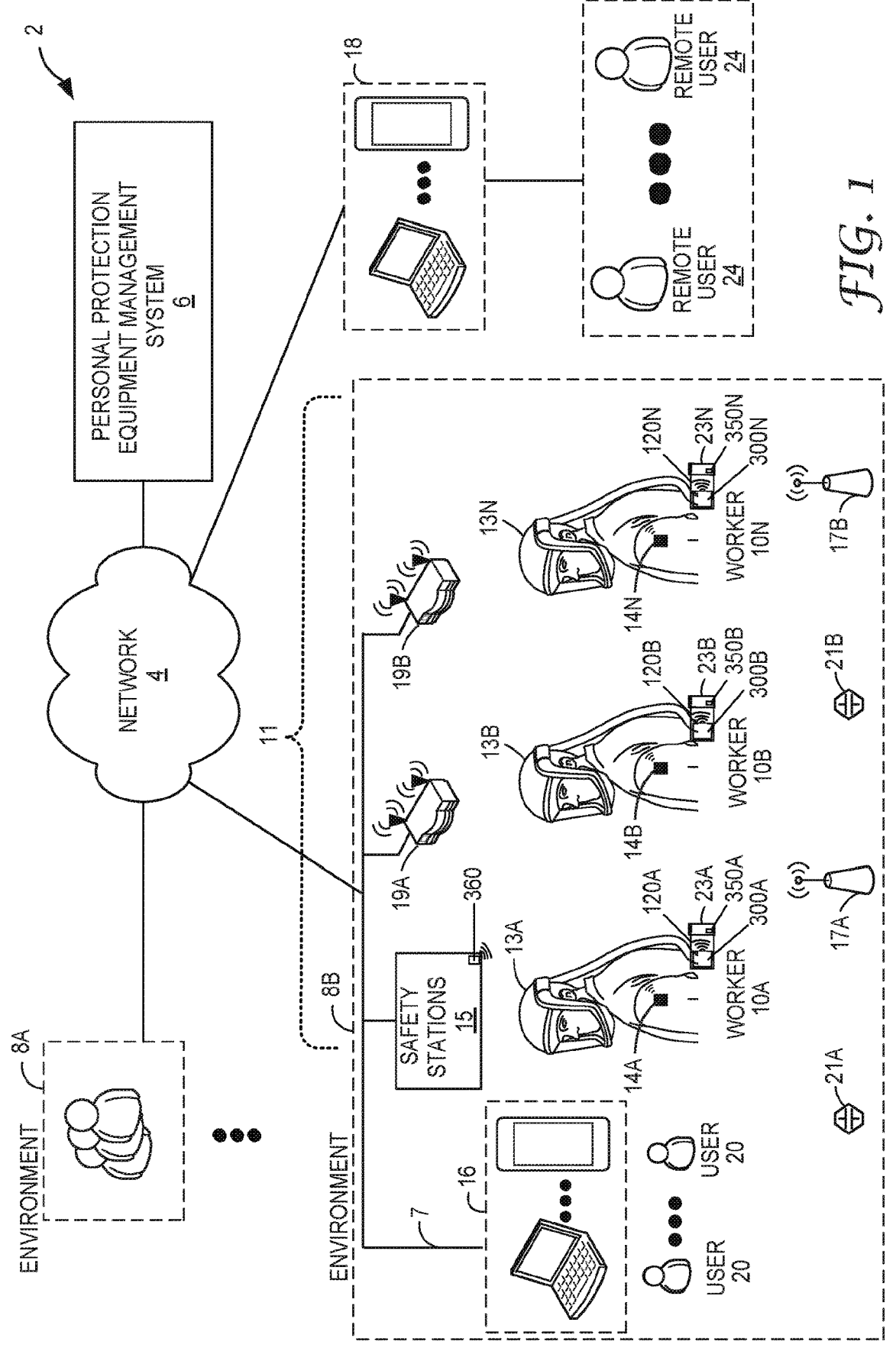
FIG. 1 is a block diagram illustrating an example system that includes a digital change management policy (DCMP) system, in accordance with some techniques of this disclosure.

It is to be understood that the embodiments may be utilized and structural changes may be made without departing from the scope of the invention. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

In general, a worker in a work environment may be exposed to various hazards or safety events (e.g., air contamination, heat, falls, etc.). Regulations may require the worker to wear one or more articles of personal protective equipment (PPE) to protect the worker from these hazards and safety events. For example, a respirator may include a removable filter cartridge to filter hazardous chemicals or other contaminants out of the air before it may be inhaled by a worker.

In some examples, a contaminant capture cartridge or filter cartridge includes a wirelessly-accessible electronic data-storage unit, such as an electronic chip or chipset configured to encode or otherwise store data for use by a computing device or system. In one example, the electronic chip or chipset is configured to encode a digital change management policy (DCMP) indicating a useful lifespan of the cartridge, so that the cartridge may be replaced at the end of the useful lifespan. For example, a computing system may store a set of customized DCMPs (e.g., one or more usage policies for each model type of cartridge) within a centralized (e.g., cloud-based) repository. The computing system may wirelessly access a model number or other data stored within the electronic chip or chipset integrated within a given filter cartridge in order to retrieve a particular DCMP from the centralized repository and encode the DCMP within the electronic chips of any cartridges of that model type. In some examples, a particular DCMP may also be location-specific, such as tailored to comply with local safety regulations of a geographic region where the filter cartridge is intended to be used.

In another example, the computing system may encode data within the electronic chip indicating an actual amount of use of the cartridge. For example, the computing device may periodically update the actual amount of use within the electronic chip while the cartridge is installed within a respirator. Based on the actual amount of use and the DCMP, the computing system may periodically determine a remaining useful lifespan of the cartridge, for example, an amount of use remaining before the cartridge needs to be replaced, according to the DCMP. In some examples, the computing system may determine that the actual amount of use of the cartridge is above a predetermined threshold amount of use (e.g., above 90% of the useful lifespan of the cartridge), and output a notification that the cartridge may need to be replaced.

The example systems described herein may include a PPE management system and, in some examples, may be integrated with the PPE management system to improve resource management and worker safety, and provide technical advantages over other systems by, for example, discouraging a user from replacing the filter cartridges too early (e.g., before the full useful lifespan has been expended), thereby reducing waste of precious resources, and additionally, by discouraging the user from replacing the filter cartridges too late (e.g., after the filters have begun to exhibit reduced performance), thereby increasing the health and safety of the worker using the respirator.

As another example, the articles, systems, and techniques described herein may help enable a PPE management system to, prior to the occurrence of a safety event, alert that corrective action need be taken. For instance, the computing systems described herein may be able to identify expired or expended filter cartridges, and may communicate with a PPE management system to distribute messages, alerts and other communications to various devices operated by safety managers and other users within a work environment.

FIG. 1 is a block diagram illustrating an example computing system 2 that includes a digital change management policy (DCMP) system 11 for managing the use and replacement of removable (e.g., disposable) contaminant capture cartridges 23A-23N (collectively, "contaminant capture cartridges 23," also referred to herein as "filter cartridges 23"). DCMP system 11 includes at least one respirator 13A having at least one replaceable contaminant capture cartridge 23A, and a computing device (e.g., communication hub 14A, safety station 15, respirator-integrated computing device 300A, or another computing device) configured to perform one or more techniques of this disclosure. In various examples, DCMP system 11 may be a component of, or communicatively connected to, a personal protective equipment management system (PPEMS) 6.

In general, DCMP system 11, either as part of, or in conjunction with, PPEMS 6, is configured to manage and/or monitor an amount of use of contaminant capture cartridge 23A for respirator 13A, according to techniques described in this disclosure. More specifically, respirator 13A includes at least one contaminant capture cartridge 23A having a data-storage device 350A, such as an electronic chip or chipset (e.g., an RFID tag).

DCMP system 11 is configured to retrieve, from a centralized (e.g., cloud-based) data repository (e.g., PPEMS 6), a cartridge-specific and environment-specific usage policy, such as a tailored useful-lifespan indication, and encode the usage policy onto the electronic chip 350A. In some examples, DCMP system 11 also encodes usage data, indicating an actual (e.g., current) amount of use of the cartridge, onto electronic chip 350. One or more computing devices of DCMP 11 (e.g., safety station 15, PPEMS 6, communication hubs 14, PPE computing device 300, among others) utilize the DCMPs along with the usage data read from electronic chips 350 of cartridges 23 to manage a filter cartridge inventory and/or detect or predict safety events associated with respirators 13. As used in this disclosure, "safety events" may refer to the exhaustion or near-exhaustion of the useful lifespan of a contaminant capture cartridge 23 of a respirator 13. For example, according to techniques of this disclosure, the one or more computing devices of DCMP system 11 monitor an amount of usage of contaminant capture cartridges 23 of respirators 13 and determine, based on DCMPs of the cartridges 23, whether one or more of the contaminant capture cartridges 23 (e.g., a particulate filter) is due for replacement.

As shown in the example of FIG. 1, system 2 represents a computing environment in which computing device(s) within a plurality of physical environments 8A, 8B (collectively, "environments 8") electronically communicate with PPEMS 6 via one or more computer networks 4. Each of physical environment 8 represents a physical environment, such as a work environment, in which one or more individuals, such as workers 10, utilize personal protective equipment 13 while engaging in tasks or activities within the respective environment. Example environments 8 include construction sites, mining sites, manufacturing sites, among others.

In this example, environment 8A is shown as generally as having workers 10, while environment 8B is shown in expanded form to provide a more detailed example. In the example of FIG. 1, a plurality of workers 10A-10N are shown as utilizing personal protective equipment (PPE), such as respirators 13. Respirators 13 in the example of FIG. 1 are illustrated as powered air-purifying respirators (PA-PRs), having a facepiece configured to form a sealed area over at least a nose and mouth of a user, and an air blower coupled to the facepiece by a hose to supply air to the sealed area. In other examples, respirators 13 may include negative-pressure reusable respirators (NPRRs), in which the air pressure inside the facepiece is less than the ambient air pressure (e.g., the pressure of the air outside the respirator) during inhalation.

In some examples, respirators 13 are configured to receive contaminant capture cartridges 23A-23N (collectively, contaminant "capture cartridges 23"). Contaminant capture cartridges 23 are configured to remove contaminants from air as air passes through the contaminant capture cartridge, for example, when blown by an air blower device 120 of respirator 13, or when a worker 10 wearing a reusable respirator 13 inhales air through the cartridge 23. Contaminant capture cartridges 23 include particulate filters, chemical cartridges, or combination particulate filters/chemical cartridges. As used throughout this disclosure, particulate filters are configured to protect a worker from particulates (e.g., dust, mists, fumes, smoke, mold, bacteria, etc.). Particulate filters capture particulates through impaction, interception, and/or diffusion. As used throughout this disclosure, chemical cartridges are configured to protect a worker from gases or vapors. Chemical cartridges may include sorbent materials (e.g., activated carbon) that react with a gas or vapor to capture the gas or vapor and remove the gas or vapor from air to be breathed by a worker. For instance, chemical cartridges may capture organic vapors, acid gasses, ammonia, methylamine, formaldehyde, mercury vapor, chlorine gas, among others.

Contaminant capture cartridges 23 are removable. In other words, a worker may remove a contaminant capture cartridge from respirator 13 (e.g., upon the contaminant capture cartridge reaching the end of its expected useful lifespan) and install a different (e.g., unused, new) contaminant capture cartridge to the respirator. In some examples, the particulate filters or chemical cartridges have a limited service life. In some examples, when a chemical cartridge is exhausted (e.g., captures a threshold amount of gas or vapors), gases or vapors may pass through the chemical cartridge to the worker (which is called "breakthrough"). In some examples, as particulate filters become saturated with a contaminant, the filter becomes harder to pull air through, thus making the worker inhale deeper to breathe.

In some examples, respirators 13 may include one or more output devices for outputting data that is indicative of operation of respirator 13 and/or generating and outputting communications to the respective worker 10. For example, respirators 13 may include one or more devices to generate audible feedback (e.g., one or more speakers), visual feedback (e.g., one or more displays, light emitting diodes (LEDs) or the like), or tactile feedback (e.g., a device that vibrates or provides other haptic feedback).

Each of respirators 13 is configured to communicate data, such as sensed motions, events and conditions, via wireless communications, such as via 802.11 Wi-Fi® protocols, Bluetooth® protocol or the like. Respirators 13 may, for example, communicate directly with a wireless access point 19. As another example, each worker 10 may be equipped with a respective one of wearable communication hubs 14A-14N (collectively, "communication hubs 14," also referred to herein as "data hubs 14") that enable and facilitate communication between respirators 13 and PPEMS 6. For example, respirators 13 as well as other PPEs (such as fall protection equipment, hearing protection, hardhats, or other equipment) for the respective worker 10 may communicate with a respective communication hub 14 via Bluetooth or other short-range wireless communication protocol, and the communication hubs may communicate with PPEMS 6 via wireless communications processed by wireless access points 19. Although shown as wearable devices, communication hubs 14 may be implemented as stand-alone devices deployed within environment 8B. In some examples, communication hubs 14 may be articles of PPE. In other examples, each respirator 13 may include an integrated computing device 300 configured to perform one or more of these functions.

In general, each of environments 8 include computing facilities (e.g., a local area network) by which sensing stations 21, beacons 17, and/or respirators 13 are able to communicate with PPEMS 6. For examples, environments 8 may be configured with wireless technology, such as 802.11 wireless networks, 802.15 ZigBee networks, or the like. In the example of FIG. 1, environment 8B includes a local network 7 that provides a packet-based transport medium for communicating with PPEMS 6 via network 4.

Environment 8B may include wireless access point 19 to provide support for wireless communications. In some examples, environment 8B may include a plurality of wireless access points 19 that may be geographically distributed throughout the environment to provide support for wireless communications throughout the work environment.

In some examples, each worker 10 may be equipped with a respective one of wearable communication hubs 14A-14N that enable and facilitate wireless communication between PPEMS 6 and sensing stations 21, beacons 17, and/or respirators 13. For example, sensing stations 21, beacons 17, and/or respirators 13 may communicate with a respective communication hub 14 via wireless communication (e.g., Bluetooth® or other short-range protocol), and the communication hubs 14 may communicate with PPEMS 6 via wireless communications processed by wireless access point 19. Although shown as wearable devices, communication hubs 14 may be implemented as stand-alone devices deployed within environment 8B.

In general, each of communication hubs 14 (or equivalently, computing devices 300) is programmable via PPEMS 6 so that local alert rules may be installed and executed without requiring a connection to the cloud. For example, in accordance with techniques of this disclosure, each hub 14 may be configured to receive and store, from PPEMS 6, a set of digital change management policies (DCMPs) for one or more replaceable or expendable items of inventory. For example, a particular DCMP may indicate a tailored policy for determining when to change or replace a disposable component of system 2, such as contaminant capture cartridges 23. As one non-limiting example, a DCMP may indicate that a particular model type of contaminant capture cartridge 23 used within a particular type of work environment (e.g., exposed to a known contaminant) within a particular geographic region (e.g., subject to the safety regulations of a particular country) is meant to be discarded and replaced after 100 hours of cumulative use within a respirator 13, in compliance with the local safety regulations. More complex examples of DCMPs may indicate, for example, that an initial time-based replacement policy (e.g., a maximum of 100 hours of use) may be dynamically shortened as the respective contaminant capture cartridge 23 is exposed to (e.g., filters) higher levels or concentrations of contamination. Communication hubs 14, safety station 15, and/or computing devices 300 may be configured to generate alerts as an actual amount of use of a contaminant capture cartridge 23 approaches (e.g., exceeds thresholds of) corresponding DCMPs. As such, each of hubs 14 provides a relay of streams of data from sensing stations 21, beacons 17, and/or respirators 13, and provides a local computing environment for localized alerting based on streams of events in the event communication with PPEMS 6 is lost.

As shown in the example of FIG. 1, an environment, such as environment 8B, may also contain one or more wireless-enabled beacons, such as beacons 17A-17B, that provide proximity data and/or accurate location data within the work environment. For example, beacons 17A-17B may be GPS-enabled such that a controller within the respective beacon may be able to precisely determine the position of the respective beacon. Based on wireless communications with one or more of beacons 17, a given respirator 13 or communication hub 14 worn by a worker 10 is configured to determine the location of the worker within environment 8B. In this way, event data reported to PPEMS 6 may be stamped with positional data to aid analysis, reporting and analytics performed by PPEMS 6. In other examples, beacons 17A-17B may be configured to output a Bluetooth Low Energy (BLE) signal such that respirator 13 or hub 14 may determine a general location within environment 8B.

In addition, an environment, such as environment 8B, may also include one or more wireless-enabled sensing stations, such as sensing stations 21A, 21B. Each sensing station 21 includes one or more sensors and a controller configured to output data indicative of sensed environmental conditions. Moreover, sensing stations 21 may be positioned within respective geographic regions of environment 8B or otherwise interact with beacons 17 to determine respective positions and include such positional data when reporting environmental data to PPEMS 6. As such, PPEMS 6 may be configured to correlate the sensed environmental conditions with the particular regions and, therefore, may utilize the captured environmental data when processing event data received from respirators 13, or sensing stations 21. For example, PPEMS 6 may utilize the environmental data to aid generating alerts or other instructions for respirators 13 and for performing predictive analytics, such as determining any correlations between certain environmental conditions (e.g., heat, humidity; visibility) with abnormal worker behavior or increased safety events. As such, PPEMS 6 may utilize current environmental conditions to aid prediction and avoidance of imminent safety events. Example environmental conditions that may be sensed by sensing stations 21 include but are not limited to temperature, humidity; presence of contaminants or other hazardous materials, pressure, visibility, wind and the like. Safety events may refer to heat-related illness or injury, cardiac-related illness or injury, respiratory-related illness or injury, or eye-related or hearing-related injury or illness.

In example implementations, an environment, such as environment 8B, may also include one or more safety stations 15 distributed throughout the environment. Safety stations 15 may allow one of workers 10 to check out respirators 13 and/or other safety equipment, verify that safety equipment is appropriate for a particular one of environments 8, and/or exchange data. Safety stations 15 may enable workers 10 to send and receive data from sensing stations 21, and/or beacons 17. For example, safety stations 15 may transmit alert rules, software updates, or firmware updates to respirators 13 or other equipment, such as sensing stations 21, and/or beacons 17. Safety stations 15 may also receive data cached on respirators 13, hubs 14, sensing stations 21, beacons 17, and/or other safety equipment. For example, safety station 15 may include an electronic reader 360 configured to read usage data and DCMP data from electronic chips 350 on cartridges 23, such as RFID chips or other wirelessly accessible electronic storage.

In addition, each of environments 8 may include computing facilities that provide an operating environment for end-user computing devices 16 for interacting with PPEMS 6 and/or DCMP system 11 via network 4. For example, each of environments 8 typically includes one or more safety managers responsible for overseeing safety compliance within the environment. In general, each user 20 interacts with computing devices 16 to access PPEMS 6. Similarly, remote users may use computing devices 18 to interact with PPEMS 6 and/or DCMP system 11 via network 4. For purposes of example, the end-user computing devices 16 may be laptops, desktop computers, mobile devices such as tablets or so-called smart phones and the like.

Users 20, 24 interact with PPEMS 6 to control and actively manage many aspects of safely equipment utilized by workers 10, such as accessing and viewing usage records, analytics and reporting. For example, users 20, 24 may review data acquired and stored by PPEMS 6, where the data may include data specifying starting and ending times over a time duration (e.g., a day, a week, etc.), data collected during particular events, such as amounts of use of various contaminant capture cartridges 23, remaining useful lifespans of contaminant capture cartridges 23, sensed data acquired from the user, environment data, and the like. In addition, users 20, 24 may interact with PPEMS 6 to perform asset tracking (e.g., inventory management) and to schedule maintenance events for individual pieces of safety equipment, e.g., contaminant capture cartridges 23 and/or respirators 13, to ensure compliance with any procedures or regulations. PPEMS 6 may allow users 20, 24 to create and complete digital checklists with respect to the maintenance procedures and to synchronize any results of the procedures from computing devices 16, 18 to PPEMS 6.

PPEMS 6 provides an integrated suite of personal protective equipment management tools and implements various techniques of this disclosure. That is, PPEMS 6 provides an integrated, end-to-end system for managing personal protective equipment (PPE), e.g., contaminant capture cartridges 23 of respirators 13, used by workers 10 within one or more physical environments 8. The techniques of this disclosure may be realized within various parts of system 2.

PPEMS 6 may integrate an event-processing platform configured to process thousands or even millions of concurrent streams of events from digitally enabled devices, such as sensing stations 21, beacons 17, respirators 13, and/or data hubs 14. An underlying analytics engine of PPEMS 6 may apply models to the inbound streams to compute assertions, such as identified anomalies or predicted occurrences of safety events based on conditions or behavior patterns of workers 10.

Further, PPEMS 6 may provide real-time alerting and reporting to notify workers 10 and/or users 20, 24 of any predicted events, anomalies, trends, and the like. The analytics engine of PPEMS 6 may, in some examples, apply analytics to identify relationships or correlations between sensed worker data, environmental conditions, geographic regions and other factors and analyze the impact on safety events. PPEMS 6 may determine, based on the data acquired across populations of workers 10, which particular activities, possibly within certain geographic regions, lead to, or are predicted to lead to, unusually high occurrences of safety events.

In this way, PPEMS 6 tightly integrates comprehensive tools for managing PPE with an underlying analytics engine and communication system to provide data acquisition, monitoring, activity logging, reporting, behavior analytics and alert generation. Moreover, PPEMS 6 provides a communication system for operation and utilization by and between the various elements of system 2. Users 20, 24 may access PPEMS 6 to view results on any analytics performed by PPEMS 6 on data acquired from workers 10. In some examples, PPEMS 6 may present a web-based interface via a web server (e.g., an HTTP server) or client-side applications may be deployed for devices of computing devices 16, 18 used by users 20, 24, such as desktop computers, laptop computers, mobile devices such as smartphones and tablets, or the like.

In some examples, PPEMS 6 may provide a database query engine for directly querying PPEMS 6 to view acquired safety data, compliance data and any results of the analytic engine, e.g., by the way of dashboards, alert notifications, reports and the like. That is, users 20, 24 or software executing on computing devices 16, 18, may submit queries to PPEMS 6 and receive data corresponding to the queries for presentation in the form of one or more reports or dashboards. Such dashboards may provide various insights regarding system 2, such as baseline ("normal") operation across worker populations, identifications of any anomalous workers engaging in abnormal activities that may potentially expose the worker to risks, identifications of any geographic regions within environments 8 for which unusually anomalous (e.g., high) safety events have been or are predicted to occur, identifications of any of environments 8 exhibiting anomalous occurrences of safety events relative to other environments, and the like.

As illustrated in detail below, PPEMS 6 may simplify workflows for individuals charged with monitoring and ensure safety compliance for an entity or environment. That is, PPEMS 6 may enable active safety management and allow an organization to take preventative or correction actions with respect to certain regions within environments 8, particular pieces of safety equipment or individual workers 10, define and may further allow the entity to implement workflow procedures that are data-driven by an underlying analytical engine.

As one example, the underlying analytical engine of PPEMS 6 may be configured to compute and present customer-defined metrics for worker populations within a given environment 8 or across multiple environments for an organization as a whole. For example, PPEMS 6 may be configured to acquire data and provide aggregated performance metrics and predicted behavior analytics across a worker population (e.g., across workers 10 of either or both of environments 8A, 8B). Furthermore, users 20, 24 may set benchmarks for occurrence of any safety incidences, and PPEMS 6 may track actual performance metrics relative to the benchmarks for individuals or defined worker populations.

As another example, PPEMS 6 may further trigger an alert if certain combinations of conditions are present, e.g., to accelerate examination or service of safety equipment, such as the replacement of a contaminant capture cartridge 23 of one of respirators 13. In this manner, PPEMS 6 may identify individual respirators 13 or workers 10 for which the metrics do not meet the benchmarks and prompt the users to intervene and/or perform procedures to improve the metrics relative to the benchmarks, thereby ensuring compliance and actively managing safety for workers 10.

In accordance with techniques of this disclosure, initially, DCMP system 11 retrieves and encodes a uniquely tailored DCMP within electronic chip or chipset 350A of contaminant capture cartridge 23A. For example, a computing device of DCMP system 11, such as communication hub 14A, safety station 15, integrated computing device 300A, or another computing device, includes an electronic reader 360 configured to interrogate electronic chip 350A of contaminant capture cartridge 23A. electronic chip 350A may encode a model number or other indicator of a specific type of contaminant cartridge 23A. The computing device of DCMP system 11 may use the model number to query a centralized data repository, such as PPEMS 6, to retrieve a particular DCMP for that cartridge 23A. The retrieved DCMP may be both cartridge-specific (e.g., tailored to that model type of cartridge 23) as well as context-specific. For example, the DCMP may be tailored to comply with local safety regulations for the geographic region in which environment 8B is located. Further, the DCMP may be tailored based on the unique type of environment 8B, such as to address or account for particular types and/or amounts of contamination known to be encountered within environment 8B. For example, a geographic-region indicator and/or a work-environment indicator may be included along with the cartridge model number within the query of PPEMS 6. Upon receiving the specific DCMP from PPEMS 6, the one or more computing devices of DCMP system 11 may encode, via antenna 360, the DCMP locally within electronic chip 350A of cartridge 23A

In further accordance with techniques of this disclosure, DCMP system 11 determines whether a contaminant capture cartridge 23 of a respirator 13 is due for replacement. For example, each contaminant capture cartridge 23 includes a data-storage unit, such as an electronic chip or chipset 350, that is configured to store information indicative of the respective contaminant capture cartridge 23. In some examples, an electronic chip or chipset 350 includes a radio frequency identifier (RFID) tag. In other examples, electronic chip 350 includes another electronically erasable programmable read-only memory (EEPROM) component, or a non-volatile read-only random-access memory (NVRAM) component. Furthermore, under the umbrella of EEPROM chips, there are both active and passive options. The scope of this disclosure encompasses both active and passive EEPROM components. As one illustrative example, electronic chip 350 includes a "dual port" near-field communication (NFC) tag with an attached EEPROM memory unit.

In some examples, electronic chip 350 is configured to store at least a digital change management policy (DCMP) for the respective contaminant capture cartridge. For example, a DCMP may include a policy (e.g., a set of rules defining one or more criteria) for determining a useful lifespan of the respective contaminant capture cartridge 23, such as a threshold amount of usage of cartridge 23 before the cartridge 23 should be replaced. In some examples, but not all examples, the electronic chip 350 may further store data indicating an actual or current amount of use of the respective cartridge 23. For example, a computing device, such as communication hub 14, safety station 15, integrated computing device 300, or a different computing device, may periodically update the stored data indicating the actual amount of use of cartridge 23 within the electronic chip 350.

In some examples, DCMP system 11 (e.g., a computing device of DCMP system 11) may periodically read the DCMP data and the actual usage data from the electronic chip 350 to determine whether cartridge 23 should be replaced. For example, a computing device of DCMP system 11 may determine whether the actual amount of use of cartridge 23 exceeds a predetermined threshold amount of the preferred useful lifespan of cartridge 23, as indicated by the DCMP stored in the electronic chip 350 coupled to or embedded within cartridge 23. Responsive to determining that the actual amount of use exceeds the predetermined threshold, DCMP system 11 is configured to generate and output an alert or other notification, thereby informing one of users 20, 24 or workers 10 that cartridge 23 is due to be replaced.

In some examples, contaminant capture cartridge 23A includes a chemical cartridge and environment 8B includes a sensing station 21A configured to detect the concentration of one or more contaminants (e.g., gases or vapors) in work environment 8B. In such examples, DCMP system 11 may determine whether contaminant capture cartridge 23A should be replaced based at least in part on the concentration of the contaminant and an amount of time worker 10A is located with environment 8B (e.g., an amount of time that cartridge 23 is exposed to the contaminant). For example, DCMP system 11 may determine a threshold protection time (e.g., an amount of time that contaminant capture cartridge 23A protects worker 10A) based on DCMP data stored within the electronic chip 350A for the contaminant capture cartridge 23A and the contamination concentration. For example, the DCMP data within electronic chip 350 may indicate a model type of contaminant capture cartridge 23A (e.g., a model number indicating a model type), and an amount of contaminant that the contaminant capture cartridge 23A can capture (also referred to as a contaminant-capture capacity), among other data. For instance, DCMP system 11 may determine the threshold protection time based on the contaminant-capture capacity of contaminant capture cartridge 23A and the contaminant concentration within work environment 8B. In such instances, DCMP system 11 determines whether the actual usage time (e.g., time within environment 8B) of contaminant capture cartridge 23A satisfies the threshold protection time. In some examples, DCMP system 11 determines that contaminant capture cartridge 23A is not due for replacement in response to determining that the actual usage time of contaminant capture cartridge 23A does not satisfy (e.g., is less than) the threshold protection time. As another example, DCMP system 11 determines that contaminant capture cartridge 23A is due for replacement in response to determining that the actual usage time of contaminant capture cartridge 23A satisfies (e.g., is greater than or equal to) the threshold protection time.

Responsive to determining that contaminant capture cartridge 23A is due for replacement, DCMP system 11 performs one or more actions. In one example, DCMP system 11, via PPEMS 6, outputs a notification to computing device associated with worker 10A (e.g., communication hub 14A), computing devices 16, 18 associated with users 20, 24, to safety stations 15, or other computing devices. In some examples, the notification includes data indicating the respirator 13A having the contaminant capture cartridge 23A that is due for replacement, the worker 10A associated with the respirator 13, and/or a location of the worker 10A, among other data. In some instances, a computing device (e.g., hub 14A) receives the notification and outputs an alert, for instance, by outputting an audible, visual, or tactile alert.

In some examples, DCMP system 11 controls a functionality of respirator 13 in response to determining that contaminant capture cartridge 23A is due for replacement. In one example, upon making this determination, DCMP system 11 (e.g., computing device 300A) may, for example, modify a functionality of air blower 120A of respirator 13A (such as increasing fan speed to enhance air flow, decreasing fan speed to extend the usable life of cartridge 23A, disabling respirator 30 altogether until replacement of cartridge 23A, or other operations).

While described with reference to DCMP system 11 and PPEMS 6, the functionality described in this disclosure may be performed by other computing devices, such as one or more communication hubs 14 or computing devices 300 of one or more respirators 13. For example, one or more hubs 14 may determine whether a contaminant capture cartridge 23 of a respirator 13 is due for replacement. In some examples, multiple computing devices (e.g., communication hubs 14 and respirator computer 300) may collectively perform the functionality described in this disclosure. For example, PPEMS 6 may determine a threshold protection time associated with a contaminant capture cartridge (e.g., a chemical cartridge) and one or more communication hubs 14 may determine whether the actual usage time for the contaminant capture cartridge satisfies the threshold protection time.

In this way, techniques of this disclosure may enable a computing system to more accurately or timely determine whether a contaminant capture cartridge 23 is due for replacement. The computing system may notify (e.g., in real-time) workers when a contaminant capture cartridge 23 is due for replacement, which may enable a worker to replace the contaminant capture cartridge 23. Replacing the contaminant capture cartridge 23 in a timelier manner may increase worker safety. For example, replacing a contaminant capture cartridge (e.g., a particulate filter and/or chemical cartridge) of a respirator in a timelier manner may protect the worker by preventing gases from breaking through a chemical cartridge and/or improving the ability of the worker to breathe when using a particulate filter while still protecting the worker from particulates. As another example, by storing DCMP data and/or actual usage data locally within the contaminant capture cartridge 23 to which the data pertains, DCMP system 11 reduces the likelihood of misattribution of such data, for example, reducing the likelihood that a particular DCMP or amount of actual usage data is assigned or attributed to an incorrect cartridge 23. Accordingly, the techniques of this disclosure may provide for highly accurate and efficient resource and inventory management.

Figure 2:
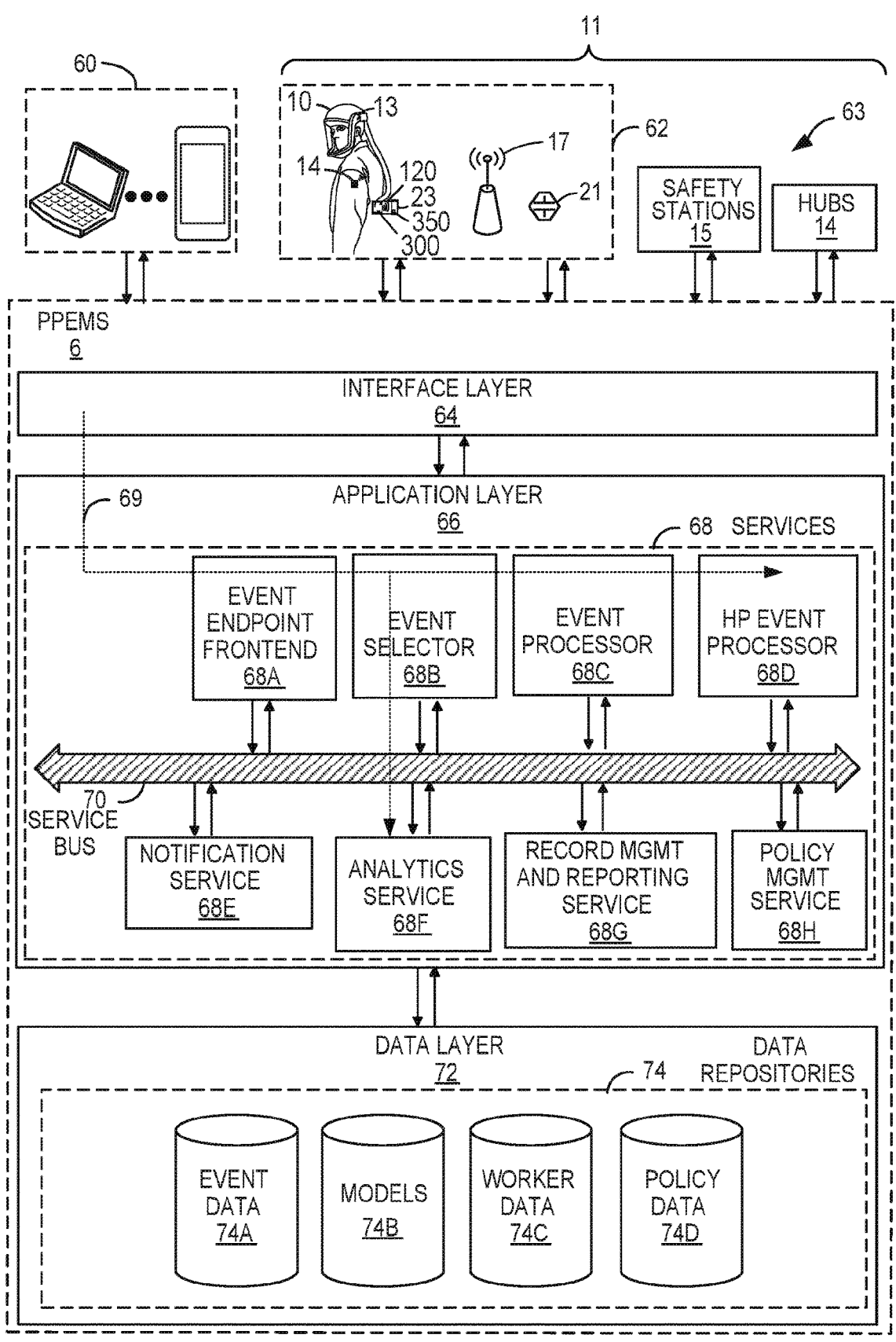
FIG. 2 is a block diagram providing an operating perspective of the system of FIG. 1 wherein the DCMP system interacts with a cloud-based PPE management system (PPEMS) to enable enhanced data processing and alerting.

FIG. 2 is a block diagram providing an operating perspective of an example in which DCMP system 11 is in communication with PPEMS 6, wherein PPEMS 6 is implemented as a cloud-based platform capable of supporting multiple, distinct access points 14 and/or work environments 8 having an overall population of workers 10 that are required to wear one or more articles of PPE. Although described with respect to PPEMS 6 the example of FIG. 2, the functionality and components of PPEMS 6 may be distributed between the PPEMS and DCMP system 11. Moreover, in some examples, DCMP system 11 may be configured to operate as a standalone system incorporating some or all of the functions described with respect to PPEMS 6 in the example of FIG. 2. For example, in accordance with the techniques of this disclosure, DCMP system 11, either alone or in combination with PPEMS 6, is configured to determine whether a contaminant capture cartridge 23 is due for replacement based at least in part on one or more useful-lifespan rules stored within an electronic chip 350 coupled to contaminant capture cartridge 23.

In the example of FIG. 2, the components of PPEMS 6 are arranged according to multiple logical layers that implement the techniques of the disclosure. Each layer may be implemented by one or more modules comprised of hardware, software, or a combination of hardware and software.

In FIG. 2, DCMP system 11 includes respirator 13 including air-blower 120 and integrated computing device 300, contaminant capture cartridge 23 having electronic chip 350, communication hub 14, and in some examples, safety stations 15, beacons 17 and sensing stations 21. Integrated computing device 300, communication hubs 14, safety stations 15, and other computing devices 60 operate as clients 63 that communicate with PPEMS 6 via interface layer 64. Computing devices 60 typically execute client software applications, such as desktop applications, mobile applications, and web applications. Computing devices 60 may represent any of computing devices 16, 18 of FIG. 1. Examples of computing devices 60 may include, but are not limited to a portable or mobile computing device (e.g., smartphone, wearable computing device, tablet), laptop computers, desktop computers, smart television platforms, and servers, to name only a few examples.

In some examples, clients 63 may communicate with PPEMS 6 via interface layer 64. For example, clients 63 may send and receive data that is retrieved, stored, generated, and/or otherwise processed by services 68. For instance, the client applications may request and edit safety event data including analytical data stored at and/or managed by DCMP system 11 and/or PPEMS 6. In some examples, client applications may request and display aggregate safety event data that summarizes or otherwise aggregates numerous individual instances of safety events and corresponding data obtained from DCMP system 11 and/or generated by PPEMS 6. The client applications may interact with PPEMS 6 to query for analytics data about past and predicted safety events, behavior trends of workers 10, to name only a few examples. In some examples, the client applications may output for display data received from PPEMS 6 to visualize such data for users of clients 63. As further illustrated and described in below, PPEMS 6 may provide data to the client applications, which the client applications output for display in user interfaces.

Client applications executing on clients 63 may be implemented for different platforms but include similar or the same functionality. For instance, a client application may be a desktop application compiled to run on a desktop operating system or a mobile application compiled to run on a mobile operating system. As another example, a client application may be a web application such as a web browser that displays web pages received from PPEMS 6. In the example of a web application, PPEMS 6 may receive requests from the web application (e.g., the web browser), process the requests, and send one or more responses back to the web application. In this way, the collection of web pages, the client-side processing web application, and the server-side processing performed by PPEMS 6 collectively provides the functionality to perform techniques of this disclosure. In this way, client applications use various services of PPEMS 6 in accordance with techniques of this disclosure, and the applications may operate within various different computing environment (e.g., embedded circuitry or processor of a PPE, a desktop operating system, mobile operating system, or web browser, to name only a few examples).

As shown in FIG. 2, PPEMS 6 includes an interface layer 64 that represents a set of application programming interfaces (API) or protocol interface presented and supported by PPEMS 6. Interface layer 64 initially receives messages from any of clients 63 for further processing at PPEMS 6. Interface layer 64 may therefore provide one or more interfaces that are available to client applications executing on clients 63. In some examples, the interfaces may be application programming interfaces (APIs) that are accessible over a network. Interface layer 64 may be implemented with one or more web servers. The one or more web servers may receive incoming requests, process and/or forward data from the requests to services 68, and provide one or more responses, based on data received from services 68, to the client application that initially sent the request. In some examples, the one or more web servers that implement interface layer 64 may include a runtime environment to deploy program logic that provides the one or more interfaces. As further described below, each service may provide a group of one or more interfaces that are accessible via interface layer 64.

In some examples, interface layer 64 may provide Representational State Transfer (RESTful) interfaces that use HTTP methods to interact with services and manipulate resources of PPEMS 6. In such examples, services 68 may generate JavaScript Object Notation (JSON) messages that interface layer 64 sends back to the client application 61 that submitted the initial request. In some examples, interface layer 64 provides web services using Simple Object Access Protocol (SOAP) to process requests from client applications 61. In still other examples, interface layer 64 may use Remote Procedure Calls (RPC) to process requests from clients 63. Upon receiving a request from a client application to use one or more services 68, interface layer 64 sends the data to application layer 66, which includes services 68.

As shown in FIG. 2, PPEMS 6 also includes an application layer 66 that represents a collection of services for implementing much of the underlying operations of PPEMS 6. Application layer 66 receives data included in requests received from client applications and further processes the data according to one or more of services 68 invoked by the requests. Application layer 66 may be implemented as one or more discrete software services executing on one or more application servers, e.g., physical or virtual machines. That is, the application servers provide runtime environments for execution of services 68. In some examples, the functionality of interface layer 64 as described above and the functionality of application layer 66 may be implemented at the same server.

Application layer 66 may include one or more separate software services 68, e.g., processes that communicate, e.g., via a logical service bus 70 as one example. Service bus 70 generally represents logical interconnections or set of interfaces that allows different services to send messages to other services, such as by a publish/subscription communication model. For instance, each of services 68 may subscribe to specific types of messages based on criteria set for the respective service. When a service publishes a message of a particular type on service bus 70, other services that subscribe to messages of that type will receive the message. In this way, each of services 68 may communicate data to one another. As another example, services 68 may communicate in point-to-point fashion using sockets or other communication mechanisms. Before describing the functionality of each of services 68, the layers are briefly described herein.

Data layer 72 of PPEMS 6 represents a data repository that provides persistence for data in PPEMS 6 using one or more data repositories 74. A data repository, generally, may be any data structure or software that stores and/or manages data. Examples of data repositories include but are not limited to relational databases, multi-dimensional databases, maps, and hash tables, to name only a few examples. Data layer 72 may be implemented using Relational Database Management System (RDBMS) software to manage data in data repositories 74. The RDBMS software may manage one or more data repositories 74, which may be accessed using Structured Query Language (SQL). Data in the one or more databases may be stored, retrieved, and modified using the RDBMS software. In some examples, data layer 72 may be implemented using an Object Database Management System (ODBMS), Online Analytical Processing (OLAP) database or other suitable data management system.

As shown in FIG. 2, each of services 68A-68H (collectively, services 68) is implemented in a modular form within PPEMS 6. Although shown as separate modules for each service, in some examples the functionality of two or more services may be combined into a single module or component. Each of services 68 may be implemented in software, hardware, or a combination of hardware and software. Moreover, services 68 may be implemented as standalone devices, separate virtual machines or containers, processes, threads or software instructions generally for execution on one or more physical processors. In some examples, one or more of services 68 may each provide one or more interfaces that are exposed through interface layer 64. Accordingly, client applications of clients 63 may call one or more interfaces of one or more of services 68 to perform techniques of this disclosure.

In some examples, services 68 may include an event processing platform including an event endpoint frontend 68A, event selector 68B, event processor 68C, high priority (HP) event processor 68D, notification service 68E, and analytics service 68F. Event endpoint frontend 68A operates as a frontend interface for exchanging communications with data hubs 14, safety stations 15, and/or respirator 13. In other words, event endpoint frontend 68A operates as a frontline interface to safety equipment deployed within environments 8 and utilized by workers 10. In some instances, event endpoint frontend 68A may be implemented as a plurality of tasks or jobs spawned to receive individual inbound communications of event streams 69 that include data sensed and captured by DCMP system 11. For instance, event streams 69 may include sensor data, such as PPE sensor data from one or more respirators 13 and environmental data from one or more sensing stations 21. When receiving event streams 69, for example, event endpoint frontend 68A may spawn tasks to quickly enqueue an inbound communication, referred to as an event, and close the communication session, thereby providing high-speed processing and scalability: Each incoming communication may, for example, carry recently captured data representing sensed conditions, motions, temperatures, actions or other data, generally referred to as events. Communications exchanged between the event endpoint frontend 68A and DCMP system 11 and/or hubs 14 may be real-time or pseudo real-time depending on communication delays and continuity.

Event selector 68B operates on the stream of events 69 received from DCMP system 11 (e.g., hubs 14) via frontend 68A and determines, based on rules or classifications, priorities associated with the incoming events. For example, safety rules may indicate that incidents of incorrect equipment for a given environment, expired or expended PPE, incorrect usage of PPEs, or lack of sensor data associated with a worker's vital signs, are to be treated as high-priority events. Based on the priorities, event selector 68B enqueues the events for subsequent processing by event processor 68C or high priority (HP) event processor 68D. Additional computational resources and objects may be dedicated to HP event processor 68D so as to ensure responsiveness to critical events, such as incorrect usage of PPEs, lack of vital signs, and the like. Responsive to processing high-priority events, HP event processor 68D may immediately invoke notification service 68E to generate alerts, instructions, warnings or other similar messages to be output to respirator 13, hubs 14, or devices used by users 20, 24. Events not classified as high priority are consumed and processed by event processor 68C.

In general, event processor 68C or high-priority (HP) event processor 68D operate on the incoming streams of events to update event data 74A within data repositories 74. In general, event data 74A may include all or a subset of data generated by DCMP system 11. For example, in some instances, event data 74A may include entire streams of data obtained from respirator 13, sensing stations 21, etc. In other instances, event data 74A may include a subset of such data, e.g., associated with a particular time period. Event processors 68C, 68D may create, read, update, and delete event data stored in event data 74A. Event data may be stored in a respective database record as a structure that includes name/value pairs of data, such as data tables specified in row/column format. For instance, a name (e.g., column) may be "workerID" and a value may be an employee identification number. An event record may include data such as, but not limited to a worker identification, acquisition timestamp(s) and sensor data. For example, event stream 69 for one or more sensors associated with a given worker (e.g., worker 10A) may be formatted as follows:

{"eventTime": "2015-12-31T18: 20:53.1210933Z",
"workerID": "00123",
"RespiratorType": "Model 600",
"ContaminantCaptureCartridge Type": "P90X",
"ContaminantCaptureCartridgeDCMP": "ITNSY46",
"AirPressurePSI": 14.0}.

In some examples, event stream 69 include category identifiers (e.g., "eventTime", "workerID", "RespiratorType", "ContaminantCaptureCartridge Type", "ContaminantCaptureCartridgeDCMP", and "AirPressurePSI"), as well as corresponding values for each category. In accordance with the techniques of this disclosure, a portion or all of event data 74A may be stored within an electronic chip or chipset 350 coupled to a contaminant capture cartridge 23, which may be installed within one of respirators 13.

In some examples, analytics service 68F is configured to perform in-depth processing of the incoming stream of events to perform real-time analytics. In this way, stream analytic service 68F may be configured to detect anomalies, transform incoming event data values, trigger alerts upon detecting safety concerns based on conditions or worker behaviors. In addition, stream analytic service 68F may generate output for communicating to DCMP system 11, such as to safety stations 15, hubs 14, or computing devices 60.

Record management and reporting service (RMRS) 68G processes and responds to messages and queries received from computing devices 60 via interface layer 64. For example, record management and reporting service 68G may receive requests from client computing devices for event data related to individual workers, populations or sample sets of workers, geographic regions of environments 8 or environments 8 as a whole, individual or groups (e.g., types) of safety equipment. In response, record management and reporting service 68G accesses event information based on the request. Upon retrieving the event data, record management and reporting service 68G constructs an output response to the client application that initially requested the information. In some examples, the data may be included in a document, such as an HTML document, or the data may be encoded in a JSON format or presented by a dashboard application executing on the requesting client computing device. For instance, as further described in this disclosure, example user interfaces that include the event information are depicted in the figures.

As additional examples, record management and reporting service 68G may receive requests to find, analyze, and correlate PPE event information. For instance, record management and reporting service 68G may receive a query request from a client application for event data 74A over a historical time frame, such as a user can view PPE event information over a period of time and/or a computing device can analyze the PPE event information over the period of time.

In accordance with techniques of this disclosure, a computing device of DCMP system 11 (e.g., data hub 14, safety station 15, or respirator-integrated computing device 300) accesses PPEMS 6 and receives a subset of change management policies that is selected based on the requirements of the respective work environment 8 (FIG. 1) of DCMP system 11. For example, application layer 66 includes change policy management service 68H, configured to receive a query from DCMP system 11 and retrieve, based on the query, one or more DCMPs stored within policy data repository 74D. Policy data repository 74D may store a plurality of different change management policies for different contaminant capture cartridges 23. The different change management policies of policy data 74D may vary based on any or all of: (1) different manufacturers of cartridges 23, (2) different model types of cartridges 23, (3) different levels of contaminant-capture capacity of cartridges 23 (e.g., different capacities for contaminant exposure), (4) different types of contaminants, and/or (5) for different geographic regions for use of cartridges 23 (e.g., according to different local health and safety regulations). An illustrative example of change management policy data 74D appears in Table 1:

TABLE 1

| Illustrative example of digital change management policies (DCMPs) stored within policy data 74D. | | | | | |
|---|---|---|---|---|---|
| Mfr. | Cartridge Model | Contaminant | Concentration Level | Region | Useful Lifespan of Cartridge |
| 3M | P90A | Chlorine Gas | 10 ppm | USA | 100 hrs |
| 3M | P90A | Chlorine Gas | 50 ppm | USA | 20 hrs |
| 3M | P90A | Chlorine Gas | 100 ppm | USA | 10 hrs |

In some examples, change policy management service 68H may receive a query from DCMP system 11 specifying a geographic location and/or a type of work environment 8. Based on this query, change policy management service 68H may determine a subset of all of the change management policies stored within policy data 74D that meet the criteria of the query. Change policy management service 68H may retrieve the appropriate subset of DCMPs from policy data 74D and download them to the requesting computing device of DCMP system 11, for subsequent programming into any cartridges 23 located within the corresponding geographic location or work environment.

In further accordance with techniques of this disclosure, analytics service 68F determines whether contaminant capture cartridge 23 of a respirator 13 is due for replacement. In one example, analytics service 68F determines whether a contaminant capture cartridge 23 of respirator 13 is due for replacement based at least in part on usage data and the DCMP stored within electronic chip 350 coupled to contaminant capture cartridge 23, which may be installed within respirator 13.

Although other technologies can be used, in some examples, but not all examples, the one or more rules (e.g., the DCMP for cartridge 23) may be generated using machine learning prior to being encoded within electronic chip 350. For example, a DCMP may include one or more general or high-level rules for determining a useful lifespan of contaminant capture cartridge 23, however, analytics service 68F may utilize machine learning in order to determine a specific implementation (e.g., specific criteria) of the general rules. In a general example, as detailed further below, a DCMP may initially indicate a useful lifespan of contaminant capture cartridge 23 in terms of a number of hours of actual use, such as 100 hours of actual use, as a non-limiting example. However, the rules of the DCMP may also indicate that this number of hours of actual use may be reduced when cartridge 23 is in the extended presence of relatively high levels (e.g., concentrations) of contamination (e.g., as indicated by one or more gas or vapor sensors), such that the cartridge's contaminant-capture or filtration capabilities are expended more quickly than an average rate of typical use. In such examples, analytics service 68F may use machine learning to dynamically update the criteria of the DCMP to account for the unpredictable conditions of the work environment.

In one example implementation, analytics service 68F utilizes machine learning when operating on event streams 69 so as to perform real-time analytics. That is, analytics service 68F may include executable code generated by application of machine learning. The executable code may take the form of software instructions or rule sets and is generally referred to as a model that can subsequently be applied to event streams 69.

Example machine learning techniques that may be employed to generate models 74B can include various learning styles, such as supervised learning, unsupervised learning, and semi-supervised learning. Example types of algorithms include Bayesian algorithms, Clustering algorithms, decision-tree algorithms, regularization algorithms, regression algorithms, instance-based algorithms, artificial neural network algorithms, deep learning algorithms, dimensionality reduction algorithms and the like. Various examples of specific algorithms include Bayesian Linear Regression, Boosted Decision Tree Regression, and Neural Network Regression, Back Propagation Neural Networks, the Apriori algorithm, K-Means Clustering, k-Nearest Neighbor (kNN), Learning Vector Quantization (LVQ), Self-Organizing Map (SOM), Locally Weighted Learning (LWL), Ridge Regression, Least Absolute Shrinkage and Selection Operator (LASSO), Elastic Net, and Least-Angle Regression (LARS), Principal Component Analysis (PCA) and Principal Component Regression (PCR).

In some examples, contaminant capture cartridge 23 of respirator 13 includes a chemical cartridge, and analytics service 68F determines whether the contaminant capture cartridge 23 is due for replacement based at least in part on sensor data from one or more sensing stations 21, as well as the DCMP for the cartridge stored within an electronic chip coupled to the cartridge. In one example, the sensor data includes data indicative of the concentration level of one or more respective gases, vapor, or other chemicals present in the air of environment 8B of FIG. 1. Analytics service 68F applies one or more rules of the DCMP stored within the electronic chip of contaminant capture cartridge 23 to the environmental sensor data generated by sensing stations 21 to determine whether contaminant capture cartridge 23 is due for replacement. For instance, analytics service 68F may determine, based on application of one or more models 74B to the environmental sensor data, a threshold exposure time (e.g., a maximum amount of time) that contaminant capture cartridge 23 provides protection. In some examples, analytics service 68F may determine an amount of time worker 10 is located within environment 8B and compare the amount of time worker 10 is located within environment 8B to the threshold exposure time to determine whether contaminant capture cartridge 23 is due for replacement. In some examples, hub 14 detects that worker 10 has entered environment 8B (e.g., based on GPS) and sends data indicating that worker 10 has entered environment 8B to PPEMS 6, such that analytics service 68F receives event data 74A (e.g., from hub 14) indicating worker 10 has entered environment 8B and tracks the time worker 10 is located within environment 8B.

In some examples, analytics service 68F dynamically determines, based at least in part on the DCMP stored in the electronic chip 350 of contaminant capture cartridge 23, an amount of cartridge 23 (e.g., a chemical cartridge) that has been consumed. For example, analytics service 68F may apply one or more models 74B to environmental sensor data from sensing stations 21 continuously or periodically to determine the amount of contaminant capture cartridge 23 consumed as conditions of environment 8B change throughout the day. In some instances, analytics service 68F determines that the concentration levels of a particular gas in environment 8B are relatively high and that a relatively high proportion (e.g., 40%) of contaminant capture cartridge 23 has been exhausted or consumed while worker 10 utilized contaminant capture cartridge 23 for a first period of time (e.g., two hours). In another instance, analytics service 68F may determine that the concentration levels of the particular gas decrease to a relatively low concentration (e.g., relative to the earlier period of time) and that a relatively low (e.g., 20%) of contaminant capture cartridge 23 was exhausted or consumed in the second period of time. In one instance, analytics service 68F determines a cumulative amount of contaminant capture cartridge 23 that has been consumed during the first and second periods of time. In some examples, analytics service 68F determines whether contaminant capture cartridge 23 is due for replacement by comparing the cumulative consumption to a threshold consumption, as indicated by the DCMP stored within the electronic chip of contaminant capture cartridge 23. As one example, analytics service 68F determines that contaminant capture cartridge 23 is due for replacement in response to determining that the cumulative consumption satisfies (e.g., is greater than) the threshold consumption or that contaminant capture cartridge 23 is not due for replacement in response to determining that the cumulative consumption does not satisfy (e.g., is less than) the threshold consumption.

Analytics service 68F generates, in some examples, separate models for individual workers, a population of workers, a particular environment, a type of respirator, a type of contaminant capture cartridge, a type of contamination, a concentration of contamination, a geographic region where respirator 13 is intended to be used, or combinations thereof. Analytics service 68F may update the models based on sensor data generated by PPE sensors or environmental sensors. For example, analytics service 68F may update the models for individual workers, a population of workers, a particular environment, a type of respirator, a type of contaminant capture cartridge, or combinations thereof based on data received from DCMP system 11.

In some examples, analytics service 68F applies one or more of models 74B to event data 74A and/or sensor data (e.g., from respirator 13 and/or sensing stations 21) to determine whether contaminant capture cartridge 23 of respirator 13 is due for replacement.

In some examples in which sensor data includes pressure data from a pressure sensor within respirator 13, analytics service 68F applies one or more models to at least the pressure data to determine whether a contaminant capture cartridge 23, such as a particulate filter, is due for replacement. Models 74B may be trained based on pressure differentials for a particular worker, worker feedback indicating worker 10 is having difficulty breathing, a type of respirator, a type of particulate filter, a type of contaminant, or a combination therein. In some examples, the one or more models 74B are trained based on physiological data (e.g., heart rate data, breathing rate data). For example, a worker may breathe heavy (e.g., thus increasing the air pressure differential) because a filter is saturated (e.g., and due for replacement) or because a worker is physically active (e.g., moving within the environment, such as walking up a set of stairs). In such examples, analytics service 68F applies one or more of models 74B to the PPE air pressure data and the physiological data to determine whether the particulate filter is saturated (e.g., such that the particulate filter is due for replacement). For example, analytics service 68F apply the models 74B to air pressure data indicating a relatively high pressure differential and physiological sensor data indicating a relatively high breathing rate and/or relatively high pulse rate, and determine based on application of the model 74B that the particulate filter is not due for replacement. In other words, analytics service 68G may infer that the worker is breathing hard because he or she is exercising rather than due to a saturated or congested particulate filter, such that analytics service 68F may determine that particulate filter 23 is not due for replacement. As another example, analytics service 68F applies the models 74B to air pressure data indicating a relatively high pressure differential and physiological sensor data indicating a relatively low breathing rate and/or relatively low pulse rate, and determine based on application of the model 74B that the particulate filter 23 is due for replacement.

As described above, analytics service 68F determines, in one example, whether contaminant capture cartridge 23 is due for replacement based on applying one or more models 74B to at least a portion of event data 74A. Models 74B may be trained based on event data 74A associated with a particular worker, a plurality of workers, the particular contaminants within the work environment 8B, a type of contaminant capture cartridge 23 utilized by the worker, or a combination therein. In some instances, the particular models 74B applied to the event data 74A for worker 10 are trained based on event data 74A for workers 10 and the models 74B applied to event data 74A for worker 10 are trained based on event data 74A for worker 10. In one example, the particular models 74B applied to the event data 74A for worker 10 are trained based on event data 74A for a plurality of workers 10. In some examples, the particular models 74B applied to the event data 74A for worker 10 are trained based on the type of contaminant capture cartridge 23 utilized by worker 10. As yet another example, the particular models 74B applied to the event data 74A for worker 10 may be trained based on contaminants within work environment 8B, while the particular models 74B applied to the event data 74A for a worker 10 within environment 8A may be trained based on contaminants within work environment 8A.

PPEMS 6 performs one or more actions in response to determining that contaminant capture cartridge 23 is due for replacement. In some examples, notification service 68E outputs a notification indicating that a contaminant capture cartridge 23 is due for replacement. For example, notification service 68E may output the notification to at least one of clients 63 (e.g., one or more of respirator 13, computing devices 60, data hubs 14, safety stations 15, or a combination therein). In one instance, the notification indicates which worker of workers 10 is associated with the article or component that is due for replacement, a location of the worker, a location at which a replacement is located, etc. As another example, notification service 68E may output a command (e.g., to a respective data hub 14 or other computing device associated with worker 10, such as a computing device 300) to output an alert indicating contaminant capture cartridge 23 is due for replacement. For example, respirator hub 14 may receive the command and may output an alert (e.g., visual, audible, haptic) to indicate contaminant capture cartridge 23 is due for replacement. While PPEMS 6 is described as determining whether contaminant capture cartridge 23 is due for replacement and performing actions, a computing device (e.g., a hub 14 or a separate computing device integrated into respirator 13) associated with a worker may perform similar functionality.

In some examples, respirator 13 includes a computing device 300 (e.g., integrated within air-blower device 120 of the respirator 13) that includes a communication device (e.g., an RFID reader) 360 (FIG. 3) configured to transmit, receive, and store information regarding a contaminant capture cartridge 23. In one example, respirator 13 includes a computing device that receives the identification information from respirator 13 and outputs the identification information to PPEMS 6. PPEMS 6 may receive the identification information (e.g., indicating a type of contaminant capture cartridge 23), determine one or more rules associated with contaminant capture cartridge 23, and determine whether the type of the contaminant capture cartridge 23 satisfies the rules. As detailed further below with respect to FIG. 3, analytics service 68F determines, for example, whether a contaminant capture cartridge 23 is installed within respirator 13, or whether the type of contaminant capture cartridge 23 is the correct type of contaminant capture cartridge 23 for the environment or hazards within the environment. As another example, a computing device associated with worker 10 (e.g., hub 14 or computing device 300 of respirator 13) may determine whether contaminant capture cartridge 23 satisfies one or more safety rules.

Figure 3:
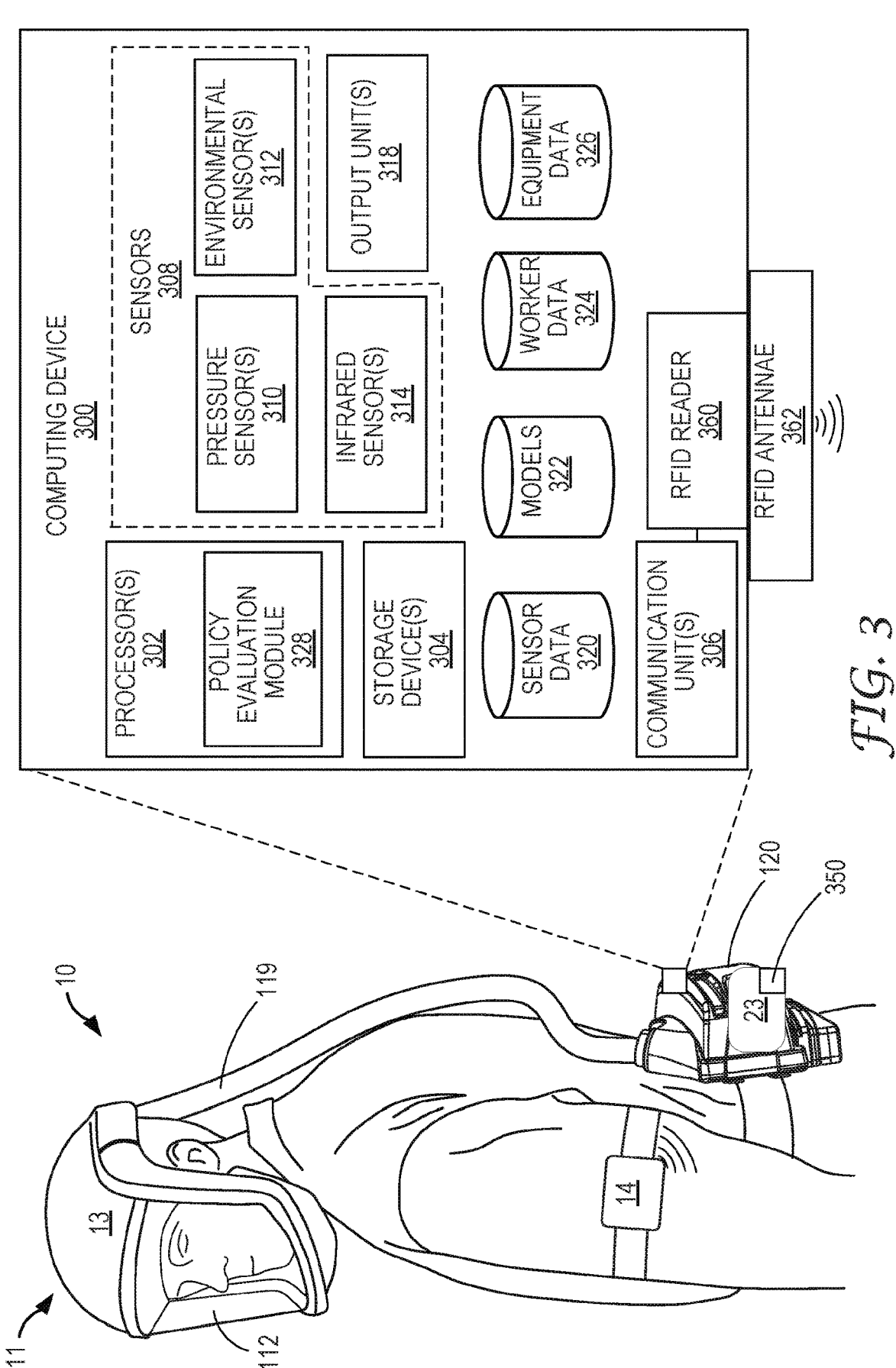
FIG. 3 is a conceptual diagram illustrating an example respirator of a DCMP system, in accordance with various techniques of this disclosure.

FIG. 3 is a conceptual diagram illustrating an example DCMP system 11 including a respirator 13, in accordance with various techniques of this disclosure. Respirator 13 is configured to receive (e.g., be physically coupled to) one or more contamination capture cartridges 23, such as a particulate filter, a chemical cartridge, or both. DCMP system 11 further includes a computing device 300. In some examples, computing device 300 is integrated within, such as physically coupled to, respirator 13. In other examples, computing device 300 comprises data hub 14 worn by worker 10. Respirator 13 includes a facepiece 112 configured to form a sealed area over a nose and mouth of a user (e.g., worker 10), and an air blower 120 coupled to facepiece 112 by a hose 119 to supply air to the sealed area. In some examples, computing device 300 is integrated within respirator 13, such as within air blower 120. In some examples, computing device 300 is physically separate from respirator 13 and communicatively coupled to respirator 13. For example, computing device 300 may be a smartphone carried by worker 10 or a data hub 14 worn by worker 10. It should be understood that the architecture and arrangement of respirator 13 and computing device 300 illustrated in FIG. 3 is shown for exemplary purposes only. In other examples, respirator 13 and computing device 300 may be configured in a variety of other ways having additional, fewer, or alternative components than those shown in FIG. 3.

In the example of FIG. 3, contaminant capture cartridge 23 includes a memory device (e.g., data-storage device), such as electronic chip (e.g., passive RFID tag) 350. electronic chip 350 stores information corresponding to contaminant capture cartridge 23, (e.g., information identifying a model type of the contaminant capture cartridge 23) and outputs the information corresponding to contaminant capture cartridge 23 in response to receiving a signal from another communication device (e.g., an RFID reader).

Computing device 300 includes one or more processors 302, one or more storage devices 304, one or more communication units 306, one or more sensors 308, one or more output units 318, sensor data 320, models 322, worker data 324, equipment data 326, policy evaluation module 328, and RFID reader 360. Processors 302, in one example, are configured to implement functionality and/or process instructions for execution within computing device 300. For example, processors 302 may be capable of processing instructions stored by storage device 304. Processors 302 may include, for example, microprocessors, digital signal processors (DSPs), application specific integrated circuits (ASICs), field-programmable gate array (FPGAs), or equivalent discrete or integrated logic circuitry.

Storage device 304 may include a computer-readable storage medium or computer-readable storage device. In some examples, storage device 304 may include one or more of a short-term memory or a long-term memory. Storage device 304 may include, for example, random access memories (RAM), dynamic random access memories (DRAM), static random access memories (SRAM), magnetic hard discs, optical discs, flash memories, or forms of electrically programmable memories (EPROM) or electrically erasable and programmable memories (EEPROM).

In some examples, storage device 304 may store an operating system or other application that controls the operation of components of computing device 300. For example, the operating system may facilitate the communication of data from electronic sensors 308 to communication unit 306. In some examples, storage device 304 is used to store program instructions for execution by processors 302. Storage device 304 may also be configured to store information within computing device 300 during operation.

Computing device 300 may use one or more communication units 306 to communicate with external devices via one or more wired or wireless connections. Communication units 306 may include various mixers, filters, amplifiers and other components designed for signal modulation, as well as one or more antennas and/or other components designed for transmitting and receiving data. Communication units 306 may send and receive data to other computing devices using any one or more suitable data communication techniques. Examples of such communication techniques may include TCP/IP, Ethernet, Wi-Fi, Bluetooth, 4G, LTE, to name only a few examples. In some instances, communication units 306 may operate in accordance with the Bluetooth Low Energy (BLE protocol. In some examples, communication units 306 may include a short-range communication unit, such as RFID reader 360 having an RFID antenna 362.

Computing device 300 includes a plurality of sensors 308 that generate sensor data indicative of operational characteristics of respirator 13, contaminant capture cartridge(s) 23, and/or an environment in which respirator 13 is used. Sensors 308 may include an accelerometer, a magnetometer, an altimeter, an environmental sensor, among other examples. In some examples, environment sensors may include one or more sensors configured to measure temperature, humidity, particulate content, gas or vapor concentration levels, or any variety of other characteristics of environments in which respirator 13 is used.

Computing device 300 includes one or more output units 318 configured to output data that is indicative of operation of respirator 13. In some examples, output unit 318 outputs data from the one or more sensors 308 of respirator 13. For example, output unit 318 may generate one or more messages containing real-time or near real-time data from one or more sensors 308 of respirator 13 for transmission to another device via communication unit 306. In some examples, output unit 318 is configured to transmit the sensor data in real-time or near-real time to PPEMS 6 (FIG. 2) or another device (e.g., a device of DCMP system 11) via communication unit 306. However, in some instances, communication unit 306 may not be able to communicate with such devices, e.g., due to conditions of an environment in which respirator 13 is located and/or network outages. In such instances, output unit 318 may cache usage data to storage device 304. That is, output unit 318 (or the sensors themselves) may send usage data to storage device 304, e.g., as sensor data 320, which may allow the usage data to be uploaded to another device upon a network connection becoming available.

In some examples, output unit 318 is configured to generate output that is perceptible by a user of respirator 13. Examples of output are audio, visual, or tactile output. For example, output units 318 include one more user interface devices including, as examples, a variety of lights, displays, haptic feedback generators, speakers or the like. Output units 318 may interpret received alert data and generate an output (e.g., an audible, visual, or tactile output) to notify a worker using respirator 13 of an alert condition (e.g., that the likelihood of a safety event is relatively high, that the environment is dangerous, that respirator 13 is malfunctioning, that one or more components of respirator 13 need to be repaired or replaced, or the like).

According to aspects of this disclosure, processors 302 utilize sensor data (e.g., data from pressure sensors 310, environmental sensors 312, and/or infrared sensors 314 of computing device 300, data from sensing stations 21 of FIG. 1, or other sensors) in a variety of ways. In some examples, processors 302 are configured to perform all or a portion of the functionality of PPEMS 6 described in FIGS. 1 and 2. While processors 302 are described as performing the functionality in FIG. 3, in some examples, other devices (e.g., PPEMS 6, hubs 14, other devices, or a combination therein) perform functionality described with reference to processors 302.

In the example of FIG. 3, computing device 300 includes sensor data 320, models 322, and worker data 324. Sensor data 320 includes data regarding operation of respirator 13, physiological conditions of worker 10A, characteristics of environment 8B, or a combination thereof. In other words, sensor data 320 may include data from PPE sensors, physiological sensors, and/or environmental sensors. Models 322 include historical data (e.g., historical sensor data) and models, such as models 74B described with reference to FIG. 2. Worker data 324 may include worker profiles, such as worker data 74C described with reference to FIG. 2.

In accordance with techniques of this disclosure, RFID reader 360 of computing device 300 is configured to read data from electronic chip 350 and/or write data onto (e.g., store data within) electronic chip 350. More specifically, computing device 300 is configured to read a digital change management policy (DCMP) from electronic chip 350, and/or write a DCMP to electronic chip 350. The DCMP includes data specifying a set of one or more rules, wherein each of the one or more rules defines a set of criteria for evaluation against input data for determining an end of the useful lifespan of the contaminant capture cartridge 350. For example, computing device 300 may further be configured to write to, and read from, electronic chip 350 usage data indicative of an actual amount of use or a current amount of use of the contaminant capture cartridge 23. In such examples, at least one of the rules of the DCMP may specify usage criteria for comparing, by policy evaluation module of processor(s) 302 of computing device 300, the actual amount of use of the contaminant capture cartridge 23 as encoded within the electronic chip 350 against a threshold amount of usage for a particular model type of contaminant capture cartridge 23.

In some examples, at least one of the rules of the DCMP specifies a threshold amount of usage for the particular model type of cartridge 23 as a first amount of time, wherein the usage data encoded within the electronic chip comprises a second amount of time recording an amount of time that the air blower 120 of the respirator has been active while the contaminant capture cartridge has been installed within the respirator.

For example, computing device 300 may be configured to receive or collect data regarding an actual amount of usage of contaminant capture cartridge 23, such as an amount of time that respirator 13 is used while contaminant capture cartridge 23 is installed within respirator 13. In one example, computing device 300 may include a clock or timer configured to monitor an amount of time that blower 120 of respirator is activated while cartridge 23 is installed within respirator 13. Either virtually continuously, or in periodic increments (e.g., every five minutes), computing device 300 may cause antenna 362 to write data to electronic chip 350 indicating the actual amount of use.

Additionally or alternatively, computing device 300 may be configured to receive or collect sensor data from environmental sensor(s) 312, such as a gas sensor or a vapor sensor, regarding an actual amount of usage of contaminant capture cartridge 23, such as an amount of a contaminant filtered by cartridge 23. In some examples, computing device 300 may determine, based on the sensor data and clock data, an amount of time that a particular contaminant capture cartridge 23 has been exposed to a particular level (e.g., concentration) of contamination while installed within respirator 13. In one example, computing device 300 may include a clock or timer configured to monitor an amount of time that blower 120 of respirator 13 is activated while cartridge 23 is installed within respirator 13. For example, either approximately continuously, or in periodic increments (e.g., every five minutes), computing device 300 may write data to electronic chip 350 indicating the actual amount of use of cartridge 23 based on the relative amount of filtered contamination and/or the length of contamination-exposure time.

In some examples, models 322 are trained on historical environmental data (e.g., indicative of gas or vapor concentration levels) generated by environmental sensors 312 or sensing stations 21 of FIG. 1 and historical determinations of contaminant capture cartridge lifespan. Processors 302 may apply models 322 to current environmental sensor data to determine a threshold exposure time and compare an actual exposure time to the threshold exposure time to determine whether contaminant capture cartridge 23A is due for replacement. As another example, processors 302 may apply models 322 to current environmental sensor data to determine a cumulative consumption and compare the cumulative consumption to a threshold consumption to determine whether contaminant capture cartridge 23A is due for replacement.

In another example, the DCMP for a cartridge 23 may specify the useful lifespan of cartridge 23 in terms of a "shelf life" of the cartridge. In some examples, the "shelf life" of cartridge 23 may be defined as an expiration date, or in other words, a predetermined amount of time passing since a manufacture date of cartridge 23. In such examples, a date of manufacture may be encoded into electronic chip 350 at the time of manufacture, and a user may select the amount of time, and command computing device to encode the amount of time into electronic chip 350 as part of the DCMP. In such examples, computing device 300 may be configured to encode usage data within electronic chip 350 in the form of the current date for comparison to the expiration date (e.g., the date of manufacture plus the predetermined amount of time). In other examples, the "shelf life" of cartridge 23 may be defined as a predetermined amount of time passing since a first usage date of cartridge 23. In such examples, computing device 300 may be configured to encode a "date of first use" as well as a current date into electronic chip 350 as part the actual usage data for comparison to the shelf life indicated by the DCMP.

In any of the examples of this disclosure, a DCMP for a cartridge 23 may depend on (e.g., be unique for) a particular type of cartridge 23 and/or a particular work environment 8. For example, as described further below with respect to FIG. 4, computing device 300 may be configured to assign (e.g., encode) a DCMP to electronic chip 350 based on a model type of cartridge 23. For example, computing device 300 may be configured to read, from electronic chip 350, data including a model number indicative of a model type of cartridge 23. For example, a manufacturer of cartridge 23 may encode the model number within electronic chip 350 at the time of manufacture. Based on the model number, computing device may retrieve from memory a unique DCMP corresponding to that model number. For example, DCMP system 11 may store in memory a plurality of different DCMPs corresponding to various different model types of removable inventory items for a particular work environment 8 and/or geographic location. The various DCMPs may be stored within any computing device of system 2, and automatically downloaded or copied onto data hub 14, safety station 15, and/or computing device 300 of DCMP system 11, for subsequent encoding within a particular cartridge 23. In another example, computing device 300 may query PPEMS 6 to retrieve either a single particular DCMP for one cartridge 23, or a subset of all DCMPs based on a work environment 8 or geographic location. Having received the unique DCMP for the model type of cartridge 23, computing device 300 may write data encoding the DCMP onto electronic chip 350 of cartridge 23. Accordingly, in accordance with this disclosure, computing device 300 may be configured to write any or all of the following data to electronic chip 350: (1) store active use time, (2) model type, (3) manufacturer expiration, (4) digital change schedule management policy, (5) unique ID, and (6) intended region of use, but this disclosure is not limited to these data fields.

In some examples in accordance with this disclosure, and as detailed further below with respect to FIG. 5, computing device 300 is configured to read data from electronic chip 350 in order to determine when or whether to replace contaminant capture cartridge 23. For example, computing device 300 may read both the DCMP and the usage data from electronic chip 350. Policy evaluation module of processor(s) 302 may then compare the usage data to the set of one or more rules of the DCMP and determine, based on the comparison, that the actual amount of use exceeds a predetermined threshold amount of usage (e.g., a predetermined threshold amount of the useful lifespan of cartridge 23). As non-limiting examples, a first "nearly expended" threshold may include 90% of the useful lifespan of cartridge 23, as indicated by the DCMP stored in electronic chip 350. A secondary "fully expended" threshold may include 100% of the useful lifespan of cartridge 23, as indicated by the DCMP stored in electronic chip 350.

In such examples, computing device 300 may output a relevant notification, and additionally or alternatively, share the data with PPEMS 6 (e.g., with notification service 68E of PPEMS 6 of FIG. 2) such that PPEMS 6 may output a notification. Additionally or alternatively, PPEMS 6 may use the above-usage-threshold determination as part of a PPE inventory management system. For example, upon determining that cartridge 23 is nearly or fully depleted, PPEMS 6 may consult a PPE inventory database to determine a remaining number of cartridges 23 to determine whether additional cartridges 23 need to be ordered. Additionally or alternatively, computing device 300 may disable functionality of respirator 13 (e.g., disable air blower 120 of respirator 13), such that a user may not use respirator 13 while it has reduced functionality due to an expended cartridge 23.

In some examples, computing device 300 may be configured to determine whether respirator 13 has a contaminant capture cartridge 23 installed at all. For example, computing device 300 may be configured to periodically attempt to scan for electronic chip 350. If computing device 300 does not identify or recognize electronic chip 350 (e.g., receive any data from electronic chip 350), computing device 300 may determine that cartridge 23 is not present, and the wearer of respirator 13 may be at risk of a respiratory safety event, such as inhaling contamination. More specifically, processors 302 determine whether contaminant capture cartridge 23 is present (e.g., attached to respirator 13) by causing communication units 306 to emit an electronic signal and determining whether communication units 306 receive a signal that includes identification information for a contaminant capture cartridge 23. In one example, processors 302 determine that a contaminant capture cartridge 23 is not present when identification information is not received and determine that a contaminant capture cartridge 23 is present when identification information is received. If contaminant capture cartridge 23 is not present, computing device 300, either alone or in concert with PPEMS 6, may generate an alert or notification to inform the wearer or a safety manager of the absence of cartridge 23, or may disable respirator 13 until a cartridge 23 is installed.

Processors 302 determine, in some examples, whether contaminant capture device 23 satisfies a safety rule by determining whether contaminant capture device 23 is authentic. In some examples, processors 302 determine whether contaminant capture device 23A is authentic based on identification information stored within electronic chip 350, for example, a unique identification number for cartridge 23. For example, a manufacturer of contaminant capture cartridge 23 may record a unique identification number of cartridge 23 within electronic chip 350 at the time of manufacture, and also communicate the unique identification number to PPEMS 6. Processors 302 may then authenticate the contaminant capture device by comparing the received identification information to the identification number stored within electronic chip 350. For example, processors 302 may output a notification to PPEMS 6 that includes the identification information of contaminant capture device 23 and a request for PPEMS 6 to authenticate the identification information. Responsive to determining that contaminant capture device 23 is not present or is not authentic, computing device 300 may output a notification (e.g., to PPEMS 6) indicating that contaminant capture device 23 is not present or is not authentic. In some examples, output units 318 output an alert (e.g., audible, visual, haptic) indicating that contaminant capture device 23 is not present or is not authentic in response to determining that that contaminant capture device 23 is not present or is not authentic.

In some examples, processors 302 may determine whether contaminant capture cartridge 23 satisfies one or more safety rules based at least in part on data received from the contaminant capture cartridge 23. For instance, electronic chip 350 may store identification information corresponding to the contaminant capture cartridge 23A (e.g., information identifying a type of the contaminant capture cartridge 23A). Processors 302 may receive the identification information for contaminant capture cartridge 23A. For instance, models 322 may include data indicative of one or more safety rules, such as indicating the type of contaminant capture cartridge 23A associated with various hazards or environments.

Output units 318 output one or more alerts in response to determining that respirator 13 and/or contaminant capture cartridge 23 satisfy one or more safety rules associated with a particular work environment. In one example, output units 318 include one or more light sources that emit light (e.g., of one or more color) indicative of a status of contaminant capture cartridge 23. For instance, output unit 318 may output light of a first color (e.g., green) to indicate a normal status, light of a second color (e.g., yellow) to indicate contaminant capture cartridge 23 is approaching time for replacement, and a light of a third color to indicate contaminant capture cartridge 23 is due for immediate replacement.

In some examples, output units 318 output notifications to one or more other computing devices (e.g., hub 14, PPEMS 6 of FIG. 1, or both) via communication units 306. For example, the notification may include data indicating the identity of worker 10, an environment 8 in which worker 10 is located, whether one or more safety rules are satisfied, among others. In some examples, the notification may indicate that a contaminant capture cartridge 23 is due for replacement or is not present within respirator 13.

Figure 4:
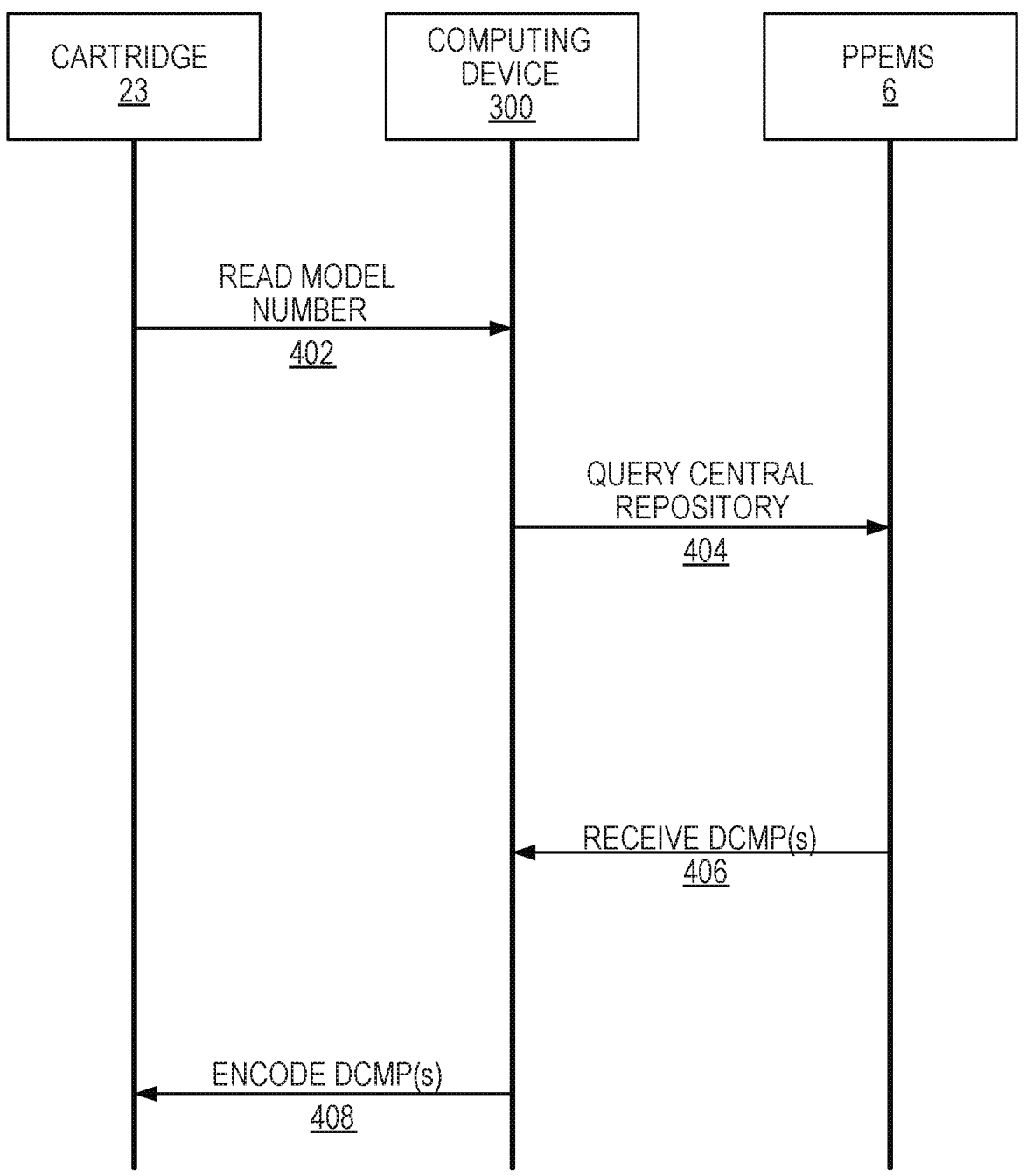
FIG. 4 is a flowchart illustrating example operations of an example computing system, in accordance with various techniques of this disclosure.

FIG. 4 is a flowchart illustrating example operations of an example computing system, in accordance with various techniques of this disclosure. FIG. 4 is described below in the context of contaminant capture cartridge 23 of respirator 13 of FIGS. 2 and 3, DCMP system 11 and PPEMS 6 of FIGS. 1 and 2, and/or computing device 300 of FIG. 3. While described in the context of respirator 13, PPEMS 6, and/or computing device 300, other computing devices (e.g., data hub 14 of FIG. 3) may perform all or a subset of the functionality described.

In some examples, a local computing device is configured to encode a digital change management policy (DCMP) onto an electronic chip 350 of a removable contaminant capture (e.g., filter) cartridge 23. For example, a computing device 300, such as a data hub 14 worn by a worker, a safety station 15, a computing device integrated into a respirator 13, or another computing device, includes an electronic reader device 360 (e.g., an RFID reader) configured to read data encoded (e.g., stored) within an electronic chip 350 of a filter cartridge 23 (402) of a respirator 13. In some examples, the data may include a model number indicating a particular model type of the cartridge 23. In some examples, the computing device may automatically read the model number from the electronic chip 350 in response to detecting that the cartridge 23 has been installed within respirator 13.

Based on the model number, the computing device retrieves a DCMP corresponding to the model number. In accordance with techniques of this disclosure, the DCMP may indicate one or more rules (e.g., policies) for determining when filter cartridge 23 is in need of replacement, for example, at the end of its useful lifespan. One example DCMP for a filter cartridge 23 may indicate that the cartridge 23 be replaced (e.g., removed and discarded) after a predetermined amount of time of actual usage. "Actual usage" as referred to herein may signify an amount of time that cartridge 23 is installed within any respirator 13, or in some cases, may signify an amount of time that cartridge 23 is installed within any respirator 13 while the respirator is activated, such as when an air blower device 120 (FIG. 3) of respirator 13 is actively forcing air through cartridge 23.

For example, the local computing device 300 may submit at least the model number as a query to a centralized repository of DCMPs, such as a cloud-based PPE management system (PPEMS) 6 (404). In response to receiving the query PPEMS 6 may transmit or download a particular DCMP or a larger subset of DCMPs to computing device 300 (406). For example, computing device 300 may retrieve a larger subset of different DCMPs (e.g., for all cartridges 23 that may be used within a particular type of work environment 8 or geographic region) from cloud-based PPEMS 6 and store them within local memory. In such examples, the local computing device may look up the a particular DCMP from within its own memory based on the model number.

In response to receiving, retrieving, or otherwise determining the DCMP for filter cartridge 23, the local computing device may encode additional data indicating the DCMP within the electronic chip 350 of the filter cartridge 23 (408). In some examples, but not all examples, the computing device 300 may further be configured to periodically encode (e.g., update) usage data within the electronic chip 350 indicating an actual or current amount of use of the particular filter cartridge 23. For example, the local computing device 300 may be configured to monitor an amount of time that filter cartridge 23 has been installed within respirator 13, and/or an amount of time that respirator 13 (e.g., an air blower device of respirator 13) has been activated while filter cartridge 23 has been installed within respirator 13. In another example, the computing device 300 may receive sensor data indicating an amount of contamination present within an environment 8 to which filter cartridge 23 has been exposed. In such examples, the computing device 300 may be configured to monitor an amount of usage based on both an amount of time that filter cartridge 23 has been exposed to the contamination, as well as a relative amount or concentration of the contamination over a corresponding time period. In periodic time increments, such as every five minutes as one illustrative example, the local computing device 300 may write data to the electronic chip 350 indicating the actual amount of usage.

Figure 5:
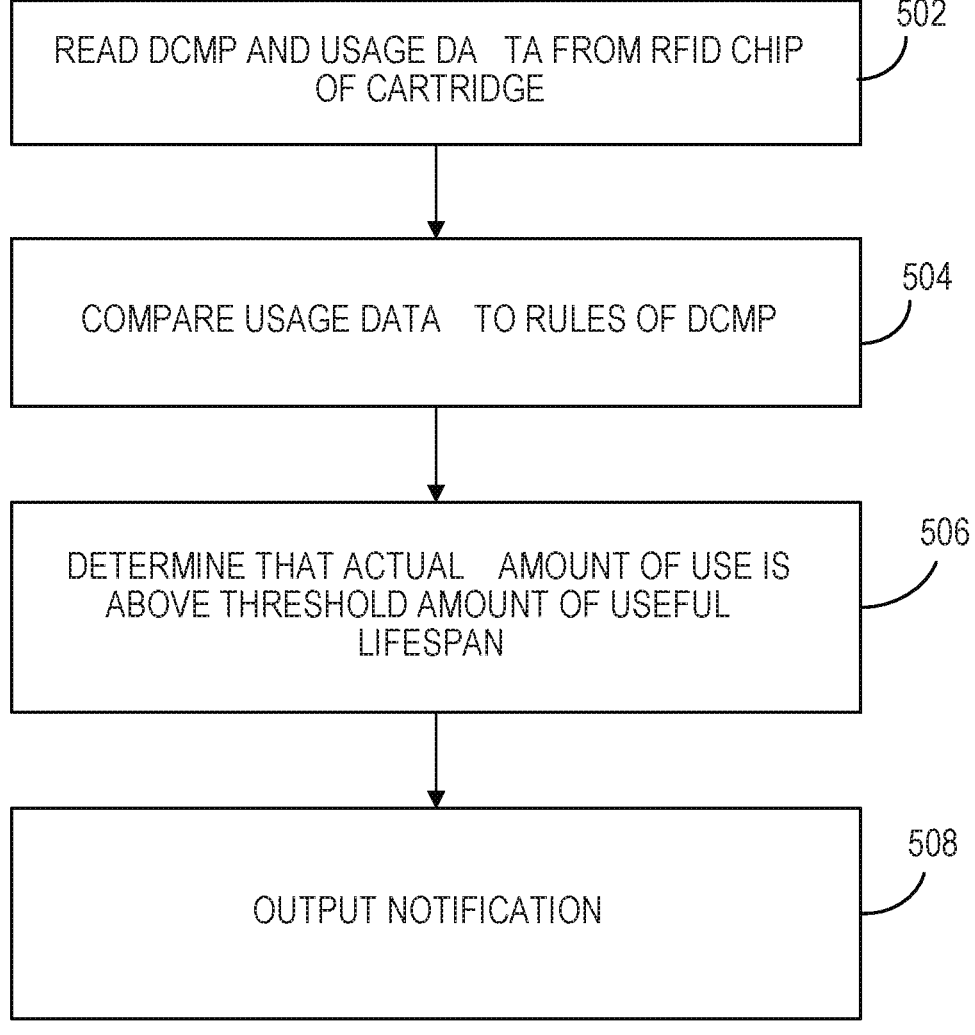
FIG. 5 is a flowchart illustrating example operations of an example computing system, in accordance with various techniques of this disclosure.

FIG. 5 is a flowchart illustrating example operations of an example computing system, in accordance with various techniques of this disclosure. FIG. 5 is described below in the context of respirator 13 of FIGS. 2 and 3, DCMP system 11 and PPEMS 6 of FIGS. 1 and 2, and/or computing device 300 of FIG. 3. While described in the context of respirator 13, DCMP system 11, PPEMS 6, and/or computing device 300, other computing devices (e.g., data hub 14 of FIG. 2) may perform all or a subset of the functionality described.

In some examples, a local computing device is configured to read data stored within an electronic chip 350 coupled to a contaminant capture (e.g., filter) cartridge 23 (502). For example, the local computing device may be configured to automatically read the data from the electronic chip 350 at a given frequency, such as every five minutes, as a non-limiting example. In another example, the local computing device may be configured to read the data from the electronic chip 350 in response to receiving user input, such as a "check data" command from a user. In some examples, the computing device may include a hub device 14 worn by a user, such as a worker 10. In other examples, the local computing device may include a safety station 15, or a computing device 300 integrated within a respirator 13 in which filter cartridge 23 is installed. In some examples in accordance with this disclosure, the data stored within the electronic chip 350 may indicate either or both of a digital change management policy (DCMP) for the filter cartridge 23 and an actual amount of use of the filter cartridge 23.

In examples in which the stored data indicates both a DCMP and an actual amount of use of filter cartridge 23, the local computing device (e.g., policy evaluation module 328 of computing device 300 of FIG. 3) may compare the actual amount of use of filter cartridge 23 to one or more rules or criteria indicated by the DCMP. As one example, the DCMP may indicate that a useful lifespan of filer cartridge 23 is approximately equal to a predetermined number of hours, such as 100 hours of use or another amount of time. The computing device may compare the actual amount of use to the useful lifespan of cartridge 23, in order to determine the actual amount of use in relation to (e.g., as a percent of) the useful lifespan.

In some cases, the local computing device may determine an above-threshold amount of actual use of filter cartridge 23 (506). For example, the DCMP may indicate one or more critical-threshold amounts of actual use relative to the useful lifespan of cartridge 23. For example, a critical threshold may indicate a percent of the useful lifespan at which to output a notification when the actual amount of use exceeds that value. As one example, the local computing device may determine that the actual use of filter cartridge 23 has exceeded 90% of the useful lifespan of filter cartridge 23. In response, the computing device may output a notification informing a user, such as worker 10 or a PPE inventory manager (e.g., via PPEMS 6), that filter cartridge 23 is nearing the end of its useful lifespan and needs to be replaced. In some cases, the DCMP may indicate more than one threshold. For example, in addition to the "90%" threshold described above, the DCMP may indicate a second threshold at 100% of the useful lifespan of filter cartridge 23. When the computing device determines that this secondary threshold has been exceeded, the computing device or PPEMS 6 may output a more urgent notification to replace filter cartridge 23, in order to protect the health of worker 10. In some examples, the local computing device may disable one or more operations of respirator 13 in order to prevent a user from using a respirator having a sub-optimal cartridge 23 installed.

The following numbered examples may illustrate one or more aspects of the disclosure:

Example 1: In some examples, a system includes a respirator comprising a facepiece configured to form a sealed area over a nose and mouth of a user and an air blower coupled to the facepiece by a hose to supply air to the sealed area: a removable contaminant capture cartridge installed within the respirator and configured to remove contaminants from the air as the air passes through the contaminant capture cartridge, wherein the contaminant capture cartridge comprises an electronic chip or chipset encoding a digital change management policy (DCMP) indicating a useful lifespan of the contaminant capture cartridge; and a computing device configured to write the DCMP onto the electronic chip or chipset: or read the DCMP from the electronic chip or chipset.

Example 2: In some examples of the system of Example, 1, the DCMP includes data specifying a set of one or more rules; and each of the one or more rules defines a set of criteria for evaluation against input data for determining an end of the useful lifespan of the contaminant capture cartridge.

Example 3: In some examples of the system of Example 2, the electronic chip further encodes usage data indicative of an actual amount of use of the contaminant capture cartridge; and at least one of the rules of the DCMP specifies usage criteria for comparing, by the computing device, the actual amount of use of the contaminant capture cartridge as encoded within the electronic chip against a threshold amount of usage for a model type of the contaminant capture cartridge.

Example 4: In some examples of the system of Example 3, at least one of the rules of the DCMP specifies the threshold amount of usage for the model type as a first amount of time; and the usage data encoded within the electronic chip comprises a second amount of time recording an amount of time that the blower of the respirator has been active while the contaminant capture cartridge has been installed within the respirator.

Example 5: In some examples of the system of Example 4, the computing device is further configured to update the second amount of time of the usage data within the electronic chip in periodic increments.

Example 6: In some examples of the system of Example 3, at least one of the rules of the DCMP specifies the threshold amount of usage for the model type as a first amount of contaminant exposure, and wherein the usage data further comprises a second amount of exposure indicative of an actual amount of contamination filtered by the contaminant capture cartridge.

Example 7: In some examples of the system of Example 6, the system further includes at least one sensor configured to determine the actual amount of contamination filtered by the contaminant capture cartridge.

Example 8: In some examples of the system of Example 7, the at least one sensor includes a gas sensor, a particulate sensor, or a vapor sensor, and the computing device is further configured to update the second amount of exposure of the usage data within the electronic chip based on sensor data from the gas sensor, the particulate sensor, or the vapor sensor.

Example 9: In some examples of the system of any of Examples 1-8, the contaminant capture cartridge includes a respirator filter cartridge configured to capture gases, particulates, or vapors.

Example 10: In some examples of the system of Example 3, the computing device is configured to compare the actual amount of use of the contaminant capture cartridge to the threshold amount of usage by: reading the DCMP and the usage data from the electronic chip: comparing the usage data to the set of one or more rules of the DCMP; and determining, based on the comparison, that the actual amount of use is above the threshold amount of usage.

Example 11: In some examples of the system of Example 10, the computing device is further configured to output, based on the determination, a notification indicating that the actual amount of use of the contaminant capture cartridge is above the threshold amount of usage.

Example 12: In some examples of the system of Example 10, the computing device is further configured to control, based on the determination, an operation of the respirator.

Example 13: In some examples of the system of Example 12, the computing device is configured to control the operation of the respirator by preventing the air blower of the respirator from activating in response to determining that the actual amount of use is above the threshold amount of usage.

Example 14: In some examples of the system of Example 10, the threshold amount of usage represents about 90% of the useful lifespan of the contaminant capture cartridge.

Example 15: In some examples of the system of Example 10, the threshold amount of usage represents 100% of the useful lifespan of the contaminant capture cartridge.

Example 16: In some examples of the system of any of Examples 1-15, the computing device is configured to write the DCMP to the electronic chip by reading, from the electronic chip, a model number indicating the model type of the contaminant capture cartridge: retrieving, from memory, the DCMP, wherein the DCMP corresponds to the model type of the contaminant capture cartridge; and encoding the DCMP within the electronic chip.

Example 17: In some examples of the system of Example 16, the computing device includes the hub device.

Example 18: In some examples of the system of any of Examples 1-16, the computing device is integrated within the air blower.

Example 19: In some examples of the system of Example 3, at least one of the rules of the DCMP specifies the threshold amount of usage for the model type as an expiration date of the contaminant capture cartridge, and the usage data comprises a current date.

Example 20: In some examples of the system of Example 3, at least one of the rules of the DCMP specifies the threshold amount of usage for the model type as an active shelf life of the contaminant capture cartridge, and the usage data encoded within the electronic chip comprises a current date and a first date indicating a date when the contaminant capture cartridge was installed into the respirator.

Example 21: In some examples of the system of any of Examples 1-20, the computing device is further configured to determine, based on the usage data, a current lifespan status of one or more items of a personal protective equipment (PPE) inventory; and manage the PPE inventory based on the current lifespan status.

Example 22: In some examples of the system of any of Examples 1-21, the computing device is further configured to determine that the contaminant capture cartridge is not installed within the respirator and output a notification indicating that the contaminant capture cartridge is not installed within the respirator.

Example 23: In some examples of the system of any of Examples 1-22, the electronic chip further encodes a unique ID of the electronic chip: or a geographic region where the contaminant capture cartridge is intended to be used.

Example 24: In some examples, a removable contaminant capture cartridge configured to be installed within a respirator is configured to remove contaminants from air as the air passes through the contaminant capture cartridge; and includes an electronic chip or chipset encoding a digital change management policy (DCMP) indicating a useful lifespan of the contaminant capture cartridge.

Example 25: In some examples, a method includes reading, by a computing device, a model number encoded within an electronic chip or chipset of a removable contaminant capture cartridge configured to be installed within a respirator: retrieving, by the computing device from a hub device: a digital change management policy (DCMP) indicating a useful lifespan of the contaminant capture cartridge; and encoding, by the computing device, the DCMP within the electronic chip.

Although the methods and systems of the present disclosure have been described with reference to specific exemplary embodiments, those of ordinary skill in the art will readily appreciate that changes and modifications may be made thereto without departing from the spirit and scope of the present disclosure.

In the present detailed description of the preferred embodiments, reference is made to the accompanying drawings, which illustrate specific embodiments in which the invention may be practiced. The illustrated embodiments are not intended to be exhaustive of all embodiments according to the invention. It is to be understood that other embodiments may be utilized and structural or logical changes may be made without departing from the scope of the present invention. The following detailed description, therefore, is not to be taken in a limiting sense, and the scope of the present invention is defined by the appended claims.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "proximate," "distal," "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above or on top of those other elements.

As used herein, when an element, component, or layer for example is described as forming a "coincident interface" with, or being "on," "connected to," "coupled with," "stacked on" or "in contact with" another element, component, or layer, it can be directly on, directly connected to, directly coupled with, directly stacked on, in direct contact with, or intervening elements, components or layers may be on, connected, coupled or in contact with the particular element, component, or layer, for example. When an element, component, or layer for example is referred to as being "directly on," "directly connected to," "directly coupled with," or "directly in contact with" another element, there are no intervening elements, components or layers for example. The techniques of this disclosure may be implemented in a wide variety of computer devices, such as servers, laptop computers, desktop computers, notebook computers, tablet computers, hand-held computers, smart phones, and the like. Any components, modules or units have been described to emphasize functional aspects and do not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

What is claimed is:

1. A system comprising:

a respirator comprising a facepiece configured to form a sealed area over a nose and mouth of a user and an air blower coupled to the facepiece by a hose to supply air to the sealed area;

a removable contaminant capture cartridge installed within the respirator and configured to remove contaminants from the air as the air passes through the contaminant capture cartridge, wherein the contaminant capture cartridge comprises an electronic chip encoding a digital change management policy (DCMP), the DCMP indicates a useful lifespan of the contaminant capture cartridge for a cartridge model number in a work environment, the electronic chip further comprises a first usage data, the first usage data comprises a cumulative amount of time that the air blower or a second air blower has been active while the contaminant capture cartridge is installed into the respirator or a second respirator; and a computing device configured to:

(i) in response to detecting installation of the contaminant capture cartridge in the respirator, read from the electronic chip a first DCMP and the first usage data;

(ii) when the first usage data indicates prior use of the contaminant capture cartridge, use the first DCMP read from the electronic chip and, during operation of the air blower, update the electronic chip on the usage data in periodic increments;

(iii) when the first usage data indicates no prior use of the contaminant capture cartridge, determine a DCMP for the contaminant capture cartridge based on the cartridge model number and the work environment, write the determined DCMP to the electronic chip, and initialize the electronic chip with the first usage data; and (iv) compare the first usage data to the DCMP and, in response to determining that a threshold portion of the useful lifespan has been expended, output an alert.

2. The system of claim 1, wherein the DCMP includes data specifying a rule; and wherein the rule defines a set of criteria for evaluation against input data for determining an end of the useful lifespan of the contaminant capture cartridge.

3. The system of claim 2, wherein the rule of the DCMP specifies usage criteria for comparing, by the computing device, the first usage data as encoded within the electronic chip against a threshold amount of usage for the cartridge model number of the contaminant capture cartridge.

4. The system of claim 3, wherein the rule of the DCMP specifies the threshold amount of usage for the cartridge model number as a first amount of contaminant exposure, and wherein second usage data further comprises a second amount of exposure indicative of an actual amount of contamination filtered by the contaminant capture cartridge.

5. The system of claim 4, wherein the system further comprises at least one sensor configured to determine the actual amount of contamination filtered by the contaminant capture cartridge.

6. The system of claim 5, wherein the at least one sensor comprises a gas sensor, a particulate sensor, or a vapor sensor, and wherein the computing device is further configured to update the second amount of exposure of the usage data within the electronic chip based on sensor data from the gas sensor, the particulate sensor, or the vapor sensor.

7. The system of claim 4, wherein the rule of the DCMP specifies the threshold amount of usage for the cartridge model number as an expiration date of the contaminant capture cartridge, and wherein a third usage data comprises a current date.

8. The system of claim 7, wherein the rule of the DCMP specifies the threshold amount of usage for the cartridge model number as an active shelf life of the contaminant capture cartridge, and wherein the third usage data encoded within the electronic chip comprises a current date and a first date indicating a date when the contaminant capture cartridge was installed into the respirator.

9. The system of claim 1, wherein the contaminant capture cartridge comprises a respirator filter cartridge configured to capture gases, particulates, or vapors.

10. The system of claim 1, wherein the computing device is further configured to control, based on the determination, an operation of the respirator by preventing the air blower of the respirator from activating in response to determining that the actual amount of use is above the threshold amount of usage.

11. The system of claim 10, wherein the threshold amount of usage comprises about 90% of the useful lifespan of the contaminant capture cartridge.

12. The system of claim 10, wherein the threshold amount of usage comprises 100% of the useful lifespan of the contaminant capture cartridge.

13. The system of claim 1, wherein the computing device comprises a hub device.

14. The system of claim 1, wherein the computing device is integrated within the air blower.

15. The system of claim 1, wherein the DCMP comprises a set of rules including at least one of: (a) a time-based rule that specifies a threshold cumulative amount of blower-active time for the cartridge model number; (b) an exposure-based rule that specifies a threshold cumulative contaminant exposure determined from a concentration and exposure duration as sensed by at least one of a gas, vapor, or particulate sensor; and (c) a shelf-life rule that specifies an expiration determined from either a manufacture date or a first-use date; and wherein the computing device is further configured to output a first alert when about 90% of the useful lifespan is reached and a second alert when 100% of the useful lifespan is reached.

16. The system of claim 1, wherein the computing device comprises a plurality of DCMPs stored in a repository.

17. The system of claim 16, wherein the cartridge comprises a wirelessly-accessible RFID chip; and a computing device including an RFID reader configured to read, from the RFID chip, the cartridge model number;

wherein the computing device is configured to retrieve, from the repository, a cartridge-specific and environment-specific DCMP corresponding to the cartridge model number and a geographic region of use or work-environment identifier.

\* \* \* \* \*